(12) United States Patent
Sagawa et al.

(10) Patent No.: US 7,135,291 B2
(45) Date of Patent: Nov. 14, 2006

(54) METHOD OF DETECTING NUCLEOTIDE POLYMORPHISM

(75) Inventors: Hiroaki Sagawa, Shiga (JP); Eiji Kobayashi, Shiga (JP); Ikunoshin Kato, Kyoto (JP)

(73) Assignee: Takara Bio Inc., Shiga (JP)

( * ) Notice: Subject to any disclaimer, the term of this patent is extended or adjusted under 35 U.S.C. 154(b) by 199 days.

(21) Appl. No.: 10/468,128

(22) PCT Filed: Feb. 14, 2002

(86) PCT No.: PCT/JP02/01222

§ 371 (c)(1), (2), (4) Date: Aug. 15, 2003

(87) PCT Pub. No.: WO02/064833

PCT Pub. Date: Aug. 22, 2002

(65) Prior Publication Data

US 2004/0137451 A1     Jul. 15, 2004

(30) Foreign Application Priority Data

| Feb. 15, 2001 | (JP) | ............................ 2001-039268 |
| Feb. 16, 2001 | (JP) | ............................ 2001-040721 |
| Mar. 30, 2001 | (JP) | ............................ 2001-101055 |
| Jun. 12, 2001 | (JP) | ............................ 2001-177381 |
| Sep. 25, 2001 | (JP) | ............................ 2001-290384 |
| Nov. 2, 2001 | (JP) | ............................ 2001-338440 |
| Dec. 3, 2001 | (JP) | ............................ 2001-368929 |

(51) Int. Cl.
*C12Q 1/68* (2006.01)
*C07H 21/02* (2006.01)
*C07H 21/04* (2006.01)

(52) U.S. Cl. ..................... 435/6; 536/23.1; 536/24.3
(58) Field of Classification Search .................. 435/6; 536/23.1, 24.3
See application file for complete search history.

(56) References Cited

U.S. PATENT DOCUMENTS

| 4,521,509 A | 6/1985 | Benkovic et al. |
| 4,683,195 A | 7/1987 | Mullis et al. |
| 4,683,202 A | 7/1987 | Mullis |
| 4,800,159 A | 1/1989 | Mullis et al. |
| 4,876,187 A | 10/1989 | Duck et al. |
| 5,137,806 A | 8/1992 | LeMasitre et al. |
| 5,210,015 A | 5/1993 | Gelfand et al. |
| 5,409,818 A | 4/1995 | Davey et al. |
| 5,455,166 A | 10/1995 | Walker |
| 5,487,972 A | 1/1996 | Gelfand et al. |
| 5,639,611 A * | 6/1997 | Wallace et al. ............... 435/6 |
| 5,660,988 A | 8/1997 | Duck et al. |
| 5,830,664 A | 11/1998 | Rosemeyer et al. |
| 5,846,717 A | 12/1998 | Brow et al. |
| 6,274,353 B1 | 8/2001 | Yang |
| 6,773,885 B1 * | 8/2004 | Walder et al. ............... 435/6 |
| 2002/0142336 A1 * | 10/2002 | Smith et al. ............... 435/6 |
| 2003/0138830 A1 * | 7/2003 | Wang et al. ............... 435/6 |

FOREIGN PATENT DOCUMENTS

| DE | 19733619 C1 | 2/2000 |
| EP | 1167524 | 1/2002 |
| EP | 1241266 | 9/2002 |
| JP | 62-190086 A | 8/1987 |
| JP | 2-504110 A | 11/1990 |
| JP | B7-114718 | 5/1995 |
| JP | 2650159 | 9/1997 |
| JP | 2001136965 | 5/2001 |
| WO | WO 89/10415 A1 | 11/1989 |
| WO | WO 00/56877 | 9/2000 |
| WO | WO 01/02559 A1 | 1/2001 |
| WO | WO 01/09343 A1 | 2/2001 |
| WO | WO 01/42498 | 6/2001 |
| WO | WO 02/00938 A2 | 1/2002 |

OTHER PUBLICATIONS

Bi et al., Nucleic Acids Research 26 (12) :3073-3075 (1998).*
Egholm, M., et al. *PNA hybridizes to complementary oligonucleotides obeying the Watson-Crick hydrogen-bonding rules.* Letters to Nature, vol. 365 (Oct. 1993), pp. 566-568.
Kobayashi, E., et al. *Atarashii Single Nucleotide Polymorphism (SNPs) Typing Ho.* Japanese Journal of Science and Technology for Identification, vol. 6 (Nov. 2001), pp. 73.
Lai, L., et al. *Crystal structure of archaeal RNase HII: a homologue of human major RNase H.* Structure, vol. 8, No. 8 (Jul. 2000), pp. 897-904.
Kato, et al, "$SNP_s$ Typing Gijutsu no Tenkai" Bio Venture. (Jul. 2001), vol. 1, No. 1, pp. 45-52.
Holland, et al, "Detection of Specific Polymerase Chain Reaction Product by Utilizing the 5' 3' Exonuclease Activity of *Thermus aquaticus* DNA polymerase", Proc. Natl. Acad. Sci. (Aug. 1991), vol. 88, pp. 7276-7280.
Oleykowski et al., Incision at nucleotide insertions/deletions and base pair mismatches by the SP nuclease of spinach, Biochemistry, 38:2200-2205 (1999).
Silber et al., S1 nuclease does not cleave DNA at single-base mis-matches, Biochmica et Biophysica Acta, 656:256-264 (1981).
Howard et al., Heteroduplex cleavage analysis using S1 nuclease, BioTechniques, 27:18-19 (Jul. 1999).

* cited by examiner

*Primary Examiner*—Ethan Whisenant
(74) *Attorney, Agent, or Firm*—Browdy and Neimark, PLLC

(57) ABSTRACT

A Nucleotide useful for detecting a base substitution in a gene, a method for detecting a base substitution in a gene using said Nucleotide, and a kit for the same.

18 Claims, 8 Drawing Sheets

A
1 2 3

B
1 2 3

C
1 2 3

METHOD OF DETECTING NUCLEOTIDE POLYMORPHISM

TECHNICAL FIELD

The present invention relates to a Nucleotide (an oligonucleotide to be used for the method of the present invention) useful for detecting a base substitution in a gene, a method for detecting a base substitution in a gene using said Nucleotide, and a kit for the same.

BACKGROUND ART

It is known that genetic codes contained in genomes of organism individuals belonging to the same species are not identical each other, and there are differences in base sequences called polymorphisms. Ones in which one to tens of base(s) is (are) deleted or inserted, ones in which a specific base sequence is duplicated and the like are known as polymorphisms. One in which one base is replaced by another base is called a single nucleotide polymorphism (SNP).

It is said that single nucleotide polymorphisms exist at a rate of about one per hundreds to one thousand bases. Accordingly, the number of SNPs present on a human genome is estimated to be three to ten million. Attentions are paid to SNPs as indexes for searching for genes related to diseases, or for having information about differences in susceptibilities to diseases or sensitivities to drugs (actions or side effects). Methods for detecting SNPs are under study.

Conventional means for detecting SNPs are generally classified into ones based on hybridization, ones based on primer extension and ones utilizing substrate specificities of enzymes.

The presence of a base substitution is detected by means of hybridization of a probe to a nucleic acid sample in a hybridization method. According to the method, it is necessary to determine a probe and hybridization conditions so that hybridization is influenced by a difference in one base. Therefore, it is difficult to establish a highly reproducible detection system.

A method for detecting a mutation using a cycle probe reaction as described in U.S. Pat. No. 5,660,988 is exemplified. A nucleic acid probe having a readily cleavable binding is hybridized to a nucleic acid molecule of interest in the method. If the nucleic acid molecule of interest does not have a base substitution, the probe is cleaved, whereas if the nucleic acid molecule has a base substitution, the probe is not cleaved. A base substitution is then detected by detecting and quantifying the degree of generation of a fragment released from the cleaved probe. However, if a trace amount of a target nucleic acid is to be detected according to this method, there may be a considerable time lag until reaching a level at which one can detect a cleavage product from the probe because the amount of the cleavage product is small.

A method for detecting a mutation using the TaqMan method as described in U.S. Pat. Nos. 5,210,015 and 5,487,972 exemplifies another method. A TaqMan probe to which a fluorescent dye and a quencher are attached is used in this method. Two probes (one containing a base substitution and the other containing no base substitution) are used as the TaqMan probes. The probe is hybridized to a nucleic acid molecule of interest, and a primer is extended from the upstream. The probe is cleaved due to a 5'→3' exonuclease activity of a DNA polymerase only if the nucleic acid molecule of interest does not contain a base substitution. A base substitution is then detected by detecting emitted fluorescence. However, the method has problems because the method requires a polymerase having a 5'→3' exonuclease activity, a PCR using a labeled nucleotide blocked at the 3'-terminus and a strict temperature adjustment, and it requires a long time for detection.

Methods in which an enzyme is utilized include methods in which a DNA polymerase is used. Such methods are further classified into three groups as follows: (1) methods in which a base substitution is detected based on the presence of a primer extension reaction using a primer of which the 3'-terminus anneals to a base portion for which a base substitution is to be detected as described in U.S. Pat. No. 5,137,806; (2) methods in which a base substitution is detected based on the presence of a primer extension reaction using a primer in which the base substitution site to be detected is located at the second nucleotide from the 3'-terminus as described in WO 01/42498; and (3) method in which the presence of a mutation at the site of interest and the base at the site are determined by distinguishing a base incorporated into a primer using a primer of which the 3'-terminus anneals to a base 3' adjacent to the base for which a base substitution is to be detected.

Methods in which a DNA ligase is used are known. According to the method, a base substitution is detected based on the presence of ligation of a probe to an adjacent probe. The terminal portion of the probe corresponds to the base portion for which a base substitution is to be detected.

A method in which a DNA polymerase or a DNA ligase is used may not be able to exactly detect a mismatch between a primer (or a probe) and a target nucleic acid due to a base substitution. Specifically, such an enzyme may initiate an enzymatic reaction even if the primer or the probe has a mismatch, providing erroneous results.

Because of a possible false positive due to an erroneous annealing between a target nucleic acid and a primer or an error made by a ligase or a polymerase to be used, it is necessary to control the reaction conditions (in particular, the reaction temperature) and the like very strictly, and there is a problem concerning the reproducibility.

Lastly, methods in which an enzyme having an activity of recognizing and cleaving a specific structure in a double-stranded nucleic acid is utilized such as the invader method as described in U.S. Pat. No. 5,846,717 are included. A cleavase is known as such an enzyme. It is possible to detect a base substitution by examining cleavage of a probe. The probe is designed such that it forms a structure recognized by the enzyme if a base substitution is present (or absent). However, such a method in which an enzyme having an activity of recognizing and cleaving a specific structure in a double-stranded nucleic acid is used has a problem concerning its sensitivity. Specifically, a signal sufficient for detection of a base substitution cannot be obtained from a trace amount of a nucleic acid sample since one signal is generated from one target nucleic acid molecule according to the method. It is naturally possible to enhance the signal by repeating the probe cleavage reaction, although it is necessary to amplify a target nucleic acid beforehand in order to obtain an intense signal. Thus, if a trace amount of a target nucleic acid is to be detected according to this method, there may be a considerable time lag until reaching a level at which one can detect a cleavage product from the probe because the amount of the cleavage product is small.

Since the methods have several problems as described above, a method that can be used to exactly detect a base substitution has been desired.

OBJECTS OF INVENTION

The main object of the present invention is to solve the above-mentioned problems and to provide a means for detecting a base substitution (e.g., an SNP) exactly with excellent reproducibility even if a trace amount of a nucleic acid sample is used.

SUMMARY OF INVENTION

In order to solve the problems as described above, a method that can be used to exactly detect a base substitution and obtain results as intense signals is desired.

The present inventors have prepared a Nucleotide. The Nucleotide is capable of annealing to a target nucleic acid for which a base substitution is to be detected. A DNA extension reaction from its 3'-terminus by a DNA polymerase is not initiated if the Nucleotide is in an intact state. Cleavage of the Nucleotide by a nuclease is influenced by the base sequence of the annealed template strand. Furthermore, the present inventors have established a method that can be used to detect a base substitution in a target nucleic acid exactly with high sensitivity using the Nucleotide. Thus, the present invention has been completed.

The present invention is outlined as follows. The first aspect of the present invention relates to a method for detecting the presence of a base substitution at a specific base in a target nucleic acid, the method comprising:

(1) mixing a sample containing a target nucleic acid with a Nucleotide, wherein the Nucleotide
  (A) is modified at the 3'-terminus such that extension from the terminus by a DNA polymerase does not occur;
  (B) has a base sequence capable of annealing to a region containing a specific base in the target nucleic acid; and
  (C) contains a sequence in which if there is a mismatch between the specific base and a base corresponding to the specific base in the Nucleotide in a complex composed of the Nucleotide and the target nucleic acid, the Nucleotide is not cleaved with a nuclease, and if there is no mismatch between the specific base and a base corresponding to the specific base in the Nucleotide, the Nucleotide is cleaved with a nuclease to generate a new 3'-terminus;

(2) treating the mixture with the nuclease and the DNA polymerase; and (3) detecting the presence of cleavage of the Nucleotide with the nuclease.

The following methods exemplify the method for detecting a base substitution of the first aspect: a method wherein the nuclease is a ribonuclease H, and the Nucleotide contains a ribonucleotide in the region containing the base corresponding to the specific base; and a method wherein the nuclease is a restriction enzyme, and the Nucleotide contains a recognition sequence for the restriction enzyme in the region containing the base corresponding to the specific base.

The second aspect of the present invention relates to a method for detecting a base substitution in a target nucleic acid, the method comprising:

(1) mixing a sample containing a target nucleic acid with a Nucleotide, wherein the Nucleotide
  (A) is modified at the 3'-terminus such that extension from the terminus by a DNA polymerase does not occur;
  (B) has a base sequence capable of annealing to a region containing a specific base in the target nucleic acid; and
  (C) contains a sequence in which if there is no mismatch between the specific base and a base corresponding to the specific base in the Nucleotide in a complex composed of the Nucleotide and the target nucleic acid, the Nucleotide is not cleaved with a nuclease, and if there is a mismatch between the specific base and a base corresponding to the specific base in the Nucleotide, the Nucleotide is cleaved with a nuclease to generate a new 3'-terminus;

(2) treating the mixture with the nuclease and the DNA polymerase; and (3) detecting the presence of cleavage of the Nucleotide with the nuclease.

A method wherein the nuclease is a mismatch-specific nuclease exemplifies the detection method of the second aspect.

The Nucleotide used in the detection method of the first or second aspect may have a sequence in which if there is no base substitution in the target nucleic acid, a mismatch is not generated in the complex composed of the Nucleotide and the target nucleic acid, or it may have a sequence in which if there is a base substitution in the target nucleic acid, a mismatch is not generated in the complex composed of the Nucleotide and the target nucleic acid.

The following methods exemplify embodiments of the first or second aspect: a method wherein the presence of a base substitution is determined based on the presence of an extension product generated by the action of the DNA polymerase; and a method wherein the presence of a base substitution is determined based on the presence of a fragment of a 3' portion released from the Nucleotide generated by the action of the nuclease. Furthermore, an extension product or a fragment of a 3' portion of the Nucleotide can be detected utilizing a label attached to the Nucleotide. A fluorescent substance may be used as the label. Furthermore, a Nucleotide to which a fluorescent substance and a substance capable of quenching fluorescence are attached, wherein the fluorescence is emitted upon cleavage by the nuclease or DNA extension subsequent to the cleavage may be used. In the embodiment in which the fluorescence labeled Nucleotide is used, a fluorescence polarization method may be utilized for detection.

In regard to the Nucleotide used in the method for detecting a base substitution of the first or second aspect, the modification of the Nucleotide at the 3'-terminus is exemplified by modification of the hydroxyl group at the 3-position of ribose. The Nucleotide used in the method for detecting a base substitution of the present invention may contain a nucleotide analog and/or a modified nucleotide. Although it is not intended to limit the present invention, for example, a deoxyriboinosine nucleotide, a deoxyribouracil nucleotide or the like may be preferably used as a nucleotide analog, and an ($\alpha$-S) ribonucleotide may be preferably used as a modified ribonucleotide. Furthermore, the method of the first or second aspect may further comprise a step of nucleic acid amplification in which an extension product generated by the action of the DNA polymerase is used as a template.

The third aspect of the present invention relates to a method for analyzing a genotype of an allele, the method comprising detecting a base substitution according to the method of the first or second aspect.

The fourth aspect of the present invention relates to a Nucleotide used for detecting a base substitution at a specific base in a target nucleic acid, which
  (A) is modified at the 3'-terminus such that extension from the terminus by a DNA polymerase does not occur;
  (B) has a base sequence capable of annealing to a region containing a specific base in the target nucleic acid; and (C) contains a sequence in which if there is a mismatch between the specific base and a base corresponding to the specific base in the Nucleotide in a complex composed of the Nucleotide and the target nucleic acid, the Nucleotide is not cleaved with a nuclease, and if there is no mismatch between the specific base and a base corresponding to the specific base in the Nucleotide, the Nucleotide is cleaved with a nuclease to generate a new 3'-terminus.

The following Nucleotides exemplify the Nucleotide of the fourth aspect: a Nucleotide which contains a ribonucleotide in the region containing the base corresponding to the specific base in the target nucleic acid, wherein if there is no mismatch between the specific base and the base corresponding to the specific base in the Nucleotide in a complex composed of the Nucleotide and the target nucleic acid, the Nucleotide is cleaved with a ribonuclease H; and a Nucleotide which contains a recognition sequence for a restriction enzyme in the region containing the base corresponding to the specific base in the target nucleic acid, wherein if there is no mismatch between the specific base and the base corresponding to the specific base in the Nucleotide in a complex composed of the Nucleotide and the target nucleic acid, the Nucleotide is cleaved with the restriction enzyme.

The fifth aspect of the present invention relates to a Nucleotide used for detecting a base substitution at a specific base in a target nucleic acid, which (A) is modified at the 3'-terminus such that extension from the terminus by a DNA polymerase does not occur;

(B) has a base sequence capable of annealing to a region containing a specific base in the target nucleic acid; and (C) contains a sequence in which if there is no mismatch between the specific base and a base corresponding to the specific base in the Nucleotide in a complex composed of the Nucleotide and the target nucleic acid, the Nucleotide is not cleaved with a nuclease, and if there is a mismatch between the specific base and a base corresponding to the specific base in the Nucleotide, the Nucleotide is cleaved with a nuclease to generate a new 3'-terminus.

A Nucleotide wherein if there is a mismatch between the Nucleotide and the target nucleic acid in a complex composed of the Nucleotide and the target nucleic acid, the Nucleotide is cleaved with a mismatch-specific nuclease exemplifies the Nucleotide of the fifth aspect.

The Nucleotide of the fourth or fifth aspect may have a sequence in which if there is no base substitution in the target nucleic acid, a mismatch is not generated in the complex composed of the Nucleotide and the target nucleic acid, or it may have a sequence in which if there is a base substitution in the target nucleic acid, a mismatch is not generated in the complex composed of the Nucleotide and the target nucleic acid.

The Nucleotide of the fourth or fifth aspect may have a labeled compound being attached. The position may be in a portion 3' or 5' to the cleavage site for the nuclease. For example, a fluorescent substance may be used as the labeled compound. By further attaching a substance capable of quenching fluorescence, a Nucleotide from which the fluorescence is emitted upon cleavage by the nuclease or DNA extension subsequent to the cleavage may be prepared.

In regard to the Nucleotide of the fourth or fifth aspect, the modification of the Nucleotide at the 3'-terminus is exemplified by modification of the hydroxyl group at the 3-position of ribose. The Nucleotide of the present invention may contain a nucleotide analog and/or a modified nucleotide. Although it is not intended to limit the present invention, for example, a deoxyriboinosine nucleotide, a deoxyribouracil nucleotide or the like may be preferably used as the nucleotide analog, and an (α-S) ribonucleotide may be preferably used as the modified ribonucleotide.

The sixth aspect of the present invention relates to a kit used for detecting a base substitution in a target nucleic acid, which contains the Nucleotide of the fourth or fifth aspect.

The following kits exemplify the kit of the sixth aspect: a kit which contains a nuclease and/or a DNA polymerase; a kit which further contains a reagent for detecting the presence of DNA extension; and a kit which further contains a reagent for carrying out a nucleic acid amplification method.

DETAILED DESCRIPTION OF THE INVENTION

Figure 1:
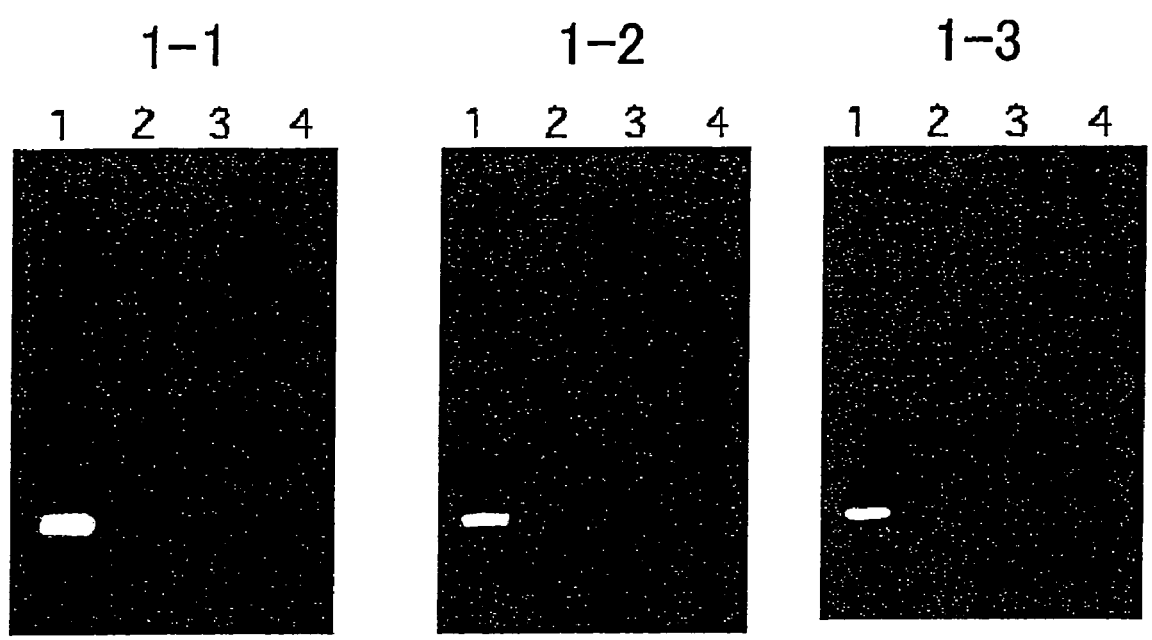
FIG. 1 illustrates results for detection of a base substitution in a human gene according to the method for detecting a base substitution of the present invention.

As used herein, "a base substitution" refers to replacement of a base at a specific site in a nucleic acid by another base. The base substitution results in a difference in genetic information among organism individuals. The difference in genetic information is called a polymorphism or a variation. The base substitutions as used herein include base substitutions in polymorphisms and variations. The base substitutions also include base substitutions artificially introduced into nucleic acids.

There is no specific limitation concerning the number of substituted bases in the base substitution. There may be one or more substitutions.

The present invention is particularly suitable for detection of a genome polymorphism or a variation, in particular, a single nucleotide polymorphism (SNP) in a gene.

The present invention is described in detail below.

(1) The Nucleotide of the Present Invention

The Nucleotide of the present invention has a base sequence capable of annealing to a region containing a site in a target nucleic acid for which a base substitution is to be detected. The Nucleotide does not serve as a primer for DNA extension by a DNA polymerase if it is in an intact state, and it can serve as a primer only if it is cleaved by a nuclease. There is no specific limitation concerning the length of the Nucleotide as long as it has the properties as described above. Both an oligonucleotide and a polynucleotide can be used according to the present invention. An oligonucleotide of usually 8 to 50 bases, preferably 10 to 40 bases, more preferably 12 to 30 bases is used as the Nucleotide of the present invention.

The Nucleotide of the present invention is usually an oligonucleotide containing deoxyribonucleotides. Optionally, it may contain a ribonucleotide, or an analog or a derivative (modification) of a nucleotide. For example, a nucleotide analog having a base such as inosine or 7-deazaguanine as its base moiety or a nucleotide analog having a ribose derivative can be used as a nucleotide analog. Examples of modified nucleotides include an (α-S) nucleotide in which the oxygen atom attached to the phosphate group is replaced by a sulfur atom, and a nucleotide to which a labeled compound is attached. Furthermore, the Nucleotide of the present invention may contain a peptide nucleic acid (PNA) as described in Nature, 365:566–568 (1993). Although it is not intended to limit the present invention, the nucleotide analog or derivative is preferably incorporated at a site at which the incorporation does not influence the action of a nuclease to be used. Incorporation of a nucleotide analog into the Nucleotide of the present invention is effective in view of suppression of higher order structure formation of the Nucleotide itself and stabilization of annealing of the Nucleotide to a target nucleic acid. Thus, the Nucleotide may contain a nucleotide analog and/or a modified nucleotide as long as the function as the Nucleotide that can be used in the method for detecting a base substitution of the present invention is retained.

The Nucleotide used according to the present invention has the following properties for detection of a base substitution at a specific base in a target nucleic acid:

(A) being modified at the 3'-terminus such that extension from the terminus by a DNA polymerase does not occur;

(B) having a base sequence capable of annealing to a region containing a specific base in the target nucleic acid; and (C) containing a sequence in which if there is a mismatch (or if there is no mismatch) between the specific base and a base corresponding to the specific base (i.e., that forms a hydrogen bond between the specific base) in the Nucleotide in a complex composed of the Nucleotide and the target nucleic acid, the Nucleotide is not cleaved with a nuclease, and if there is no mismatch (or if there is a mismatch) between the specific base and a base corresponding to the specific base in the Nucleotide, the Nucleotide is cleaved with a nuclease to generate a new 3'-terminus.

A fragment of a 5' portion of the Nucleotide cleaved with a nuclease can remain annealed to a target nucleic acid. Since a hydroxyl group exists at the 3-position of ribose or deoxyribose at the 3'-terminus of the fragment of the 5' portion of the Nucleotide, a DNA can be extended from the terminus by a DNA polymerase. Thus, the Nucleotide serves as a precursor of a primer if it has a base sequence that is cleavable with a nuclease.

As described above, the Nucleotide of the present invention is modified at the 3'-terminus such that it cannot be utilized for a DNA extension reaction by a DNA polymerase. There is no specific limitation concerning the means of modification as long as the above-mentioned objects can be achieved. Examples thereof include addition, at the 3'-terminus, of a dideoxy nucleotide, a nucleotide modified at the hydroxyl group at the 3-position of ribose, or a nucleotide with modification that interferes with extension by a DNA polymerase due to steric hindrance. Alkylation or other known modification methods can be utilized as a method for modifying the hydroxyl group at the 3-position of ribose of a nucleotide. For example, a DNA extension reaction can be prevented by aminoalkylation.

The Nucleotide of the present invention has a base sequence capable of annealing, under conditions used, to a region in a target nucleic acid for which a base substitution is to be detected. The Nucleotide has a sequence that is substantially complementary to a target nucleic acid, and need not have a base sequence completely complementary to the target nucleic acid as long as the detection of a substitution at the base of interest is not disturbed.

When the Nucleotide of the present invention is annealed to a target nucleic acid and incubated in the presence of an appropriate nuclease and an appropriate DNA polymerase, cleavage of the Nucleotide is influenced by the presence of a base substitution in a target nucleic acid, that is, the presence of a mismatched site in a double-stranded nucleic acid formed by annealing of the Nucleotide to a target nucleic acid. DNA extension using the target nucleic acid as a template occurs only if the Nucleotide is cleaved to generate a new 3'-terminus. Therefore, one can have information about the presence of a mismatch, or the presence of a base substitution based on the presence of DNA extension.

According to the present invention, it is possible to prepare the Nucleotide such that a mismatch is generated if there is a base substitution to be detected, and it is also possible to prepare the Nucleotide such that a mismatch is not generated if there is a base substitution. Furthermore, one can have information about the presence of a base substitution and the type of the substituted base at the same time as follows: four types of Nucleotides each having one of four types of bases placed at a position corresponding to the base of interest are prepared; and the type of the base contained in the primer that results in extension is then examined.

As described above, the Nucleotide of the present invention is converted into a primer that is capable of DNA extension as a result of cleavage with a nuclease. The portion of the Nucleotide 5' to the cleavage site for the nuclease serves as a primer for DNA extension. There is no specific limitation concerning the nuclease as long as it cleaves (or does not cleave) the Nucleotide depending on the presence of a mismatch in a double-stranded nucleic acid formed as a result of annealing of the Nucleotide to a target nucleic acid. Examples thereof include a ribonuclease H, a restriction enzyme and a mismatch-specific nuclease.

A ribonuclease H (RNase H) is an enzyme that recognizes a double-stranded nucleic acid composed of a DNA and an RNA and selectively cleaves the RNA strand. A Nucleotide that is cleaved with a ribonuclease H only if there is no mismatch can be prepared by placing a ribonucleotide at a site in the Nucleotide corresponding to the base for which a substitution is to be detected.

There is no specific limitation concerning the ribonuclease to be used according to the present invention as long as it has an activity of recognizing a double-stranded nucleic acid composed of the Nucleotide of the present invention containing a ribonucleotide and a DNA complementary thereto and selectively cleaving at the ribonucleotide portion. For example, a ribonuclease H from *Escherichia coli*, or a ribonuclease H from a thermophilic bacterium belonging to genus *Bacillus*, a bacterium belonging to genus *Thermus*, a bacterium belonging to genus *Pyrococcus*, a bacterium belonging to genus *Thermotoga* or a bacterium belonging to genus *Archaeoglobus* can be preferably used as such an enzyme. Although it is not intended to limit the present invention, the ribonuclease H preferably exhibits a high activity under the same reaction conditions as those for a DNA polymerase to be used at the same time. If the Nucleotide of the present invention is to be used in combination with a nucleic acid amplification reaction, it is preferable to use a ribonuclease H that exhibits its activity under conditions under which the reaction is carried out. For example, it is advantageous to use a heat-resistant ribonuclease H if a nucleic acid amplification reaction that involves a reaction or treatment at a high temperature (e.g., PCR) is to be utilized. For example, a ribonuclease H from *Bacillus caldotenax, Pyrococcus furiosus, Pyrococcus horikoshii, Thermococcus litoralis, Thermotoga maritima, Archaeoglobus fulgidus* or *Methanococcus jannashi* can be used as a heat-resistant ribonuclease H.

A restriction enzyme is an enzyme that recognizes a specific base sequence (of 4 to 8 bases) in a DNA and cleaves at a position within or around the sequence. If the base portion for which a substitution is to be detected overlaps with a recognition sequence for a restriction enzyme, a Nucleotide prepared to include the sequence can be used for detection of a base substitution. If a mismatch is generated between a Nucleotide and a target nucleic acid, cleavage with a restriction enzyme does not occur. One can have information about the presence of the base substitution based on the results. If such a Nucleotide is to be used, it is necessary to make the target nucleic acid insusceptible to cleavage with the restriction enzyme. It is possible to confer resistance to the restriction enzyme specifically to the target nucleic acid, for example, by methylating the specific bases using a modification methylase corresponding to the restriction enzyme to be used.

An enzyme that recognizes and cleaves a mismatch between a target nucleic acid and a Nucleotide unlike the above-mentioned two types of nucleases may be used. Mut H or the like may be used as such an enzyme.

The Nucleotide of the present invention is cleaved with the nuclease, a new 3'-terminus is generated, and DNA extension is then initiated from the terminus. There is no specific limitation concerning the DNA polymerase used in this step as long as it is capable of DNA extension from the 3'-terminus of a primer depending on the sequence of the DNA as a template. Examples thereof include *Escherichia coli* DNA polymerase I, Klenow fragment, T7 DNA polymerase, DNA polymerases from thermophilic bacteria belonging to genus *Bacillus* (Bst DNA polymerase, Bca DNA polymerase), DNA polymerases from bacteria belonging to genus *Thermus* (Taq DNA polymerase, etc.) and α-type DNA polymerases from thermophilic archaebacteria (Pfu DNA polymerase, etc.).

If the Nucleotide of the present invention is to be used in combination with a gene amplification reaction, a DNA polymerase suitable for the gene amplification reaction is selected for use.

A fragment of a 3' portion of the Nucleotide of the present invention generated as a result of cleavage with a nuclease can remain annealed to a target nucleic acid if it is sufficiently long, although it may be released from the target nucleic acid if it is short. If a DNA polymerase having a strand displacement activity is used, the fragment is dessociated from the target nucleic acid upon DNA extension by the DNA polymerase. If a DNA polymerase having a 5'→3' exonuclease activity is used, the fragment is degraded by the DNA polymerase.

Although it is not intended to limit the present invention, for example, an oligonucleotide having a structure represented by the following general formula can be used as the Nucleotide of the present invention in case where a ribonuclease H is used as a nuclease:

General formula: 5'-dNa-Nb-dNc-N'-3'

(a: an integer of 11 or more; b: an integer of 1 or more; c: 0 or an integer of 1 or more, dN: deoxyribonucleotide; N: ribonucleotide; N': a nucleotide modified such that extension by a DNA polymerase does not occur).

The portion represented by Nb in the general formula contains a base corresponding to the base as the subject of substitution detection. Furthermore, the Nucleotide may contain a nucleotide analog or a derivative (a modified nucleotide) as long as the function of the Nucleotide is not spoiled.

A Nucleotide that is a chimeric oligonucleotide represented by the general formula wherein N' is a modified deoxyribonucleotide, a is an integer of 11 or more, b=1 to 3, c=0 to 2 is exemplified. There is no specific limitation concerning the base corresponding to the base as the subject of the base substitution detection as long as it is located in the portion represented by Nb. In one embodiment of the present invention, for example, a Nucleotide in which the length of the portion represented by (dNc-N') is three bases and a base corresponding to the base for which a base substitution is to be detected is located at the 3' end of the portion represented by Nb can be preferably used. Such a Nucleotide exhibits a good specificity in regard to detection of a base substitution.

Detection of a fragment of a 3' portion released from the Nucleotide of the present invention by cleavage with a nuclease or by a product generated upon a DNA extension reaction subsequent to the cleavage (an extension product) can be facilitated and the presence of a base substitution can be conveniently confirmed by appropriately labeling the Nucleotide.

There is no specific limitation concerning the method for labeling a Nucleotide. For example, radioisotopes ($^{32}$P, etc.), dyes, fluorescent substances, luminescent substances, various ligands (biotin, digoxigenin, etc.) and enzymes can be used. The presence of a product derived from a labeled Nucleotide can be confirmed by a detection method suitable for the label. A ligand that cannot be directly detected may be used in combination with a ligand-binding substance having a detectable label. For example, a target nucleic acid can be detected with high sensitivity by using a product from a ligand-labeled Nucleotide in combination with an enzyme-labeled anti-ligand antibody and amplifying the signal.

Examples of embodiments of fluorescence labeled Nucleotides include a Nucleotide labeled with both a fluorescent substance and a substance having an action of quenching fluorescence emitted from the fluorescent substance with appropriate spacing. Such a primer does not emit fluorescence if it is in an intact state. However, it emits fluorescence if it is cleaved with a nuclease, and the fluorescent substance and the quenching substance are placed at a distance. Since such a Nucleotide emits fluorescence at the same time as the initiation of a DNA extension reaction, one can have information about the presence of a base substitution by directly observing a reaction mixture during a reaction.

(2) The Method for Detecting a Base Substitution of the Present Invention

The Nucleotide of the present invention as described in (1) above is used in the method for detecting a base substitution of the present invention and the method comprises:

(1) mixing a sample containing a target nucleic acid with the Nucleotide;

(2) treating the mixture with a nuclease and a DNA polymerase; and (3) detecting the presence of cleavage of the Nucleotide with the nuclease. The presence of a base substitution is determined based on the presence of cleavage of a Nucleotide with a nuclease according to the characteristics of the Nucleotide of the present invention as described in (1) above.

A single-stranded or double-stranded nucleic acid (DNA or RNA) can be used as a target nucleic acid in the method for detecting a base substitution of the present invention. Depending on the nuclease to be used, it may be difficult to use an RNA as a target nucleic acid. In this case, a base substitution in an RNA can be detected by preparing a cDNA using the RNA as a template and using the cDNA as a target nucleic acid.

According to the present invention, a sample containing a target nucleic acid can be used for a detection reaction.

Any sample that may possibly contain a nucleic acid or an organism such as a cell, a tissue (a biopsy sample, etc.), a whole blood, a serum, a cerebrospinal fluid, a seminal fluid, a saliva, a sputum, a urine, feces, a hair and a cell culture may be used without limitation. Although it is not intended to limit the present invention, the test sample may be subjected to the method of the present invention preferably after it is appropriately processed, for example, after it is converted into a form with which one can carry out a reaction using a DNA polymerase. Such processes include lysis of a cell as well as extraction and purification of a nucleic acid from a sample.

According to the method for detecting a base substitution of the present invention, the presence of a base substitution is determined based on the presence of cleavage of a Nucleotide to be used and the presence of a DNA extension reaction subsequent to the cleavage. There is no specific limitation concerning the method for the determination, and known means of analyzing a nucleic acid can be used. Examples of methods for determining the presence of a DNA extension reaction include the following: a method in which a generated extension product is separated for confirmation by gel electrophoresis (agarose gel, polyacrylamide gel, etc.) or capillary electrophoresis; and a method in which increase in length of an extension product is measured by mass spectrometry. In another embodiment, a method in which incorporation of a nucleotide into an extension product is determined is exemplified. In this method, one can have information about an amount of a synthesized extension product as an amount of a nucleotide triphosphate having an appropriate label incorporated into a macromolecular extension product. The amount of the generated extension product can be determined, for example, after separating the product from unreacted nucleotides by acid precipitation or gel electrophoresis. Furthermore, a method in which pyrophosphate generated upon a DNA extension reaction is detected by enzymatic means may be used.

According to the detection method of the present invention, the extension product may be further amplified using a known nucleic acid amplification reaction. Such an embodiment is useful in view of highly sensitive detection of a base substitution.

Various nucleic acid amplification methods in which a primer having a sequence complementary to a nucleic acid as a template is used can be used as the nucleic acid amplification reaction without limitation. For example, known amplification methods such as Polymerase Chain Reaction (PCR, U.S. Pat. Nos. 4,683,195, 4,683,202 and 4,800,159), Strand Displacement Amplification (SDA, JP-B 7-114718), Self-Sustained Sequence Replication (3SR), Nucleic Acid Sequence Based Amplification (NASBA, Japanese Patent No. 2650159), Transcription-Mediated Amplification (TMA), and Isothermal and Chimeric primer-initiated Amplification of Nucleic acids (ICAN, WO 00/56877) can be used. A base substitution in a target nucleic acid can be detected by using the Nucleotide of the present invention as a primer for synthesis of a DNA complementary to a DNA strand as a template in such a method.

If the method for detecting a base substitution of the present invention is carried out utilizing the above-mentioned nucleic acid amplification method, the Nucleotide of the present invention is used as at least one of the primers used in the method, and a nuclease suitable for the Nucleotide is included in the reaction system.

According to the detection of a base substitution utilizing a nucleic acid amplification reaction as described above, the presence of a base substitution can be determined based on generation of a specific amplification product by the reaction. Although it is not intended to limit the present invention, for example, gel electrophoresis, hybridization using a probe having a sequence complementary to the amplification product, a fluorescence polarization method utilizing a fluorescence labeled Nucleotide, the TaqMan method and the like can be used for the generated amplification product. In addition, detection reactions suitable for the respective gene amplification methods can be also utilized.

If base substitutions are to be analyzed using the detection method of the present invention at a genomic level, the volume of the reaction system may be made smaller and a means of increasing degree of integration may be used in combination in order to analyze a large number of base sequences. A microchip sized several by several centimeters square to fingertip on which the basic processes of the detection method or the analysis method of the present invention (e.g., extraction of a DNA from a cell, a nucleic acid amplification reaction, detection of the DNA of interest, etc.) are integrated using an up-to-date microfabrication technique may be used in combination as such a means. Optionally, processes of gel or capillary electrophoresis and hybridization with a detection probe may be combined. Such a system is called a microchip, a micro-capillary electrophoresis (CE) chip or a nanochip.

Any nucleic acid amplification reaction may be utilized in such a system as long as the DNA fragment of interest is amplified using the reaction. Although it is not intended to limit the present invention, for example, a method in which a nucleic acid can be amplified under isothermal conditions such as the ICAN method can be preferably used. The combination with such a method can simplify the system and is very preferably utilized for the above-mentioned integrated system. Furthermore, a more highly integrated system can be constructed utilizing the techniques according to the present invention.

The specificity of detection of a base substitution can be improved by including a modified nucleotide in the Nucleotide of the present invention and/or by appropriately adjusting the reaction temperature in the method of the present invention.

The Nucleotide of the present invention having a label as described in (1) above can facilitates confirmation of the presence of a DNA extension reaction, and is useful for the method for detecting a base substitution of the present invention. In this case, the presence of an extension reaction is confirmed by detecting a labeled substance derived from the Nucleotide by a method suitable for the label as described above.

For example, if the Nucleotide of the present invention to which a fluorescent substance is attached is to be used and if the label is attached to a portion that is utilized as a primer, an extension product can be detected utilizing the fluorescence. If a label is attached to a portion 3' to the cleavage site for a nuclease in a Nucleotide, the presence of an extension reaction can be detected based on dissociation of a 3' fragment from the target nucleic acid, conversion of the fragment into a smaller molecule due to a 5'→3' exonuclease activity of a DNA polymerase or the like. A fluorescence polarization method is preferably utilized for such an embodiment that involves change in molecular weight of a fluorescence labeled Nucleotide.

If the Nucleotide of the present invention which is labeled by attaching a fluorescent substance and a substance having an action of quenching fluorescence emitted from the fluorescent substance such that the fluorescence is not emitted is to be used, the fluorescence is emitted at the same time as the initiation of an extension reaction. Therefore, a base substitution can be very readily detected.

In the above-mentioned respective embodiments, by utilizing Nucleotides each having adenine (A), cytosine (C), guanine (G), thymine (T) or uracil (U) at a position corresponding to the site for which a base substitution is to be detected as well as a distinguishable different label, one can have information about the presence of a base substitution and the type of the substituted base at the same time.

The Nucleotide of the present invention can be used in a PCR for detecting a base substitution. In this case, the Nucleotide of the present invention is used in place of one of PCR primers, and a nuclease suitable for the Nucleotide is further added to a normal reaction mixture for PCR. A base substitution can be detected with high sensitivity by selecting a nuclease that is not inactivated under the conditions for the PCR.

Cells of higher animals including humans are usually diploid having a pair of chromosomes. Therefore, if a base substitution may exist for a specific base on a chromosome, there are three possible cases as follows: homozygote (homo-type) in which both chromosomes of the cell do not have a base substitution; homozygote (homo-type) in which base substitutions are present on both chromosomes; and heterozygote (hetero-type) in which only one of chromosomes has a base substitution.

It is possible to examine whether the genotype of a diploid cell or an individual having the cell is homo-type or hetero-type for a specific base in a gene by applying the method for detecting a base substitution of the present invention to a nucleic acid sample prepared from the cell. Although it is not intended to limit the present invention, for example, if the method of the present invention is carried out using Nucleotides that correspond to four types of bases and are cleaved if there is no mismatch, signals are detected as a result of cleavage of the Nucleotides for two of the Nucleotides for a nucleic acid sample derived from a cell of which the genotype is hetero-type. On the other hand, a signal is detected for only one of the Nucleotides for a nucleic acid sample derived from a cell of which the genotype is homo-type. In addition, it is possible to simultaneously determine whether the homo-type has or does not have a base substitution. As described above, the method of the present invention is useful for detection of a base substitution in an allele.

(3) The kit Used for Detecting a Base Substitution of the Present Invention

The present invention provides a kit used for detection of a base substitution according to the present invention as described above. In one embodiment, the kit contains the Nucleotide of the present invention. It may contain a set of Nucleotides each containing one of four types of bases that can be used to determine the presence of a base substitution and the type of the substituted base at the same time. Furthermore, the kit may contain a nuclease suitable for the Nucleotide, a DNA polymerase, a substrate for the DNA polymerase (dNTP), a buffer suitable for the reaction and the like. Alternatively, the kit may contain a reagent for detection of a primer-extension product. A kit containing a reagent for preparing a reaction mixture used for a nucleic acid amplification method is preferable as a kit for detecting a base substitution in combination with a nucleic acid amplification method.

EXAMPLES

The following examples further illustrate the present invention in detail but are not to be construed to limit the scope thereof.

Referential Example 1

Cloning of *Pyrococcus furiosus* RNase HII Gene (1) Preparation of Genomic DNA from *Pyrococcus Furiosus*

2 L of a medium containing 1% Tryptone (Difco Laboratories), 0.5% yeast extract (Difco Laboratories), 1% soluble starch (Nacalai Tesque), 3.5% Jamarine S Solid (Jamarine Laboratory), 0.5% Jamarine S Liquid (Jamarine Laboratory), 0.003% $MgSO_4$, 0.001% NaCl, 0.0001% $FeSO_4.7H_2O$, 0.0001% $CoSO_4$, 0.0001% $CaCl_2.7H_2O$, 0.0001% $ZnSO_4$, 0.1 ppm $CuSO_4.5H_2O$, 0.1 ppm $KAl(SO_4)_2$, 0.1 ppm $H_3BO_4$, 0.1 ppm $Na_2MoO_4.2H_2O$ and 0.25 ppm $NiCl_2.6H_2O$ was placed in a 2-L medium bottle, sterilized at 120° C. for 20 minutes, and bubbled with nitrogen gas to remove dissolved oxygen. Then, *Pyrococcus furiosus* (purchased from Deutsche Sammlung von Mikroorganismen; DSM3638) was inoculated into the medium and cultured at 95° C. for 16 hours without shaking. After cultivation, cells were collected by centrifugation.

The resulting cells were then suspended in 4 ml of 25% sucrose, 50 mM Tris-HCl (pH 8.0). 0.4 ml of a 10 mg/ml lysozyme chloride (Nacalai Tesque) aqueous solution was added thereto. The mixture was reacted at 20° C. for 1 hour. After reaction, 24 ml of a mixture containing 150 mM NaCl, 1 mM EDTA and 20 mM Tris-HCl (pH 8.0), 0.2 ml of 20 mg/ml proteinase K (Takara Shuzo), and 2 ml of a 10% sodium lauryl sulfate aqueous solution were added to the reaction mixture. The mixture was incubated at 37° C. for 1 hour.

After reaction, the mixture was subjected to phenol-chloroform extraction followed by ethanol precipitation to prepare about 1 mg of genomic DNA.

(2) Cloning of RNase HII Gene

The entire genomic sequence of *Pyrococcus horikoshii* was published [DNA Research, 5:55–76 (1998)]. The existence of a gene encoding a homologue of RNase HII (PH1650) in the genome was known (SEQ ID NO:1, the home page of National Institute of Technology and Evaluation: http://www/nite.go.jp/).

Homology between the PH1650 gene (SEQ ID NO:1) and the partially published genomic sequence of *Pyrococcus furiosus* (the home page of University of Utah, Utah Genome Center: http://www.genome.utah.edu/sequence-.html) was searched. As a result, a highly homologous sequence was found.

Primers 1650Nde (SEQ ID NO:2) and 1650Bam (SEQ ID NO:3) were synthesized on the basis of the homologous sequence.

A PCR was carried out in a volume of 100 μl using 200 ng of the *Pyrococcus furiosus* genomic DNA obtained in Referential Example 1-(1) as a template, and 20 pmol of 1650Nde and 20 pmol of 1650Bam as primers. TaKaRa Ex Taq (Takara Shuzo) was used as a DNA polymerase for the PCR according to the attached protocol. The PCR was carried out as follows: 30 cycles of 94° C. for 30 seconds, 55° C. for 30 seconds and 72° C. for 1 minute. An amplified DNA fragment of about 0.7 kb was digested with NdeI and BamHI (both from Takara Shuzo). The resulting DNA fragment was inserted between the NdeI site and the BamHI site in a plasmid vector pET3a (Novagen) to make a plasmid pPFU220.

(3) Determination of Base Sequence of DNA Fragment Containing RNase HII Gene

The base sequence of the DNA fragment inserted into pPFU220 obtained in Referential Example 1-(2) was determined according to a dideoxy method.

Analysis of the determined base sequence revealed an open reading frame presumably encoding RNase HII. The base sequence of the open reading frame is shown in SEQ ID NO:4. The amino acid sequence of RNase HII deduced from the base sequence is shown in SEQ ID NO:5.

*Escherichia coli* JM109 transformed with the plasmid pPFU220 is designated and indicated as *Escherichia coli* JM109/pPFU220, and deposited on Sep. 5, 2000 at International Patent Organism Depositary, National Institute of Advanced Industrial Science and Technology, AIST Tsukuba Central 6, 1-1, Higashi 1-Chome, Tsukuba-shi, Ibaraki-ken 305–8566, Japan under accession number FERM P-18020 and at International Patent Organism Depositary, National Institute of Advanced Industrial Science and Technology under accession number FERM BP-7654 (date of transmission to international depositary authority: Jul. 9, 2001).

(4) Preparation of Purified RNase HII Preparation

*Escherichia coil* HMS174(DE3) (Novagen) was transformed with pPFU220 obtained in Referential Example 1-(2). The resulting *Escherichia coli* HMS174(DE3) harboring pPFU220 was inoculated into 2 L of LB medium containing 100 μg/ml of ampicillin and cultured with shaking at 37° C. for 16 hours. After cultivation, cells collected by centrifugation were suspended in 66.0 ml of a sonication buffer [50 mM Tris-HCl (pH 8.0), 1 mM EDTA, 2 mM phenylmethanesulfonyl fluoride] and sonicated. A supernatant obtained by centrifuging the sonicated suspension at 12000 rpm for 10 minutes was heated at 60° C. for 15 minutes. It was then centrifuged at 12000 rpm for 10 minutes again to collect a supernatant. Thus, 61.5 ml of a heated supernatant was obtained.

The heated supernatant was subjected to RESOURSE Q column (Amersham Pharmacia Biotech) equilibrated with Buffer A [50 mM Tris-HCl (pH 8.0), 1 mM EDTA] and chromatographed using FPLC system (Amersham Pharmacia Biotech). As a result, RNase HII flowed through the RESOURSE Q column.

60.0 ml of the flow-through RNase HII fraction was subjected to RESOURSE S column (Amersham Pharmacia Biotech) equilibrated with Buffer A and eluted with a linear gradient of 0 to 500 mM NaCl using FPLC system. A fraction containing RNase HII eluted with about 150 mM NaCl was obtained.

2.0 ml of the RNase HII fraction was concentrated by ultrafiltration using Centricon-10 (Amicon). 250 μl of the concentrate was subjected to Superdex 200 gel filtration column (Amersham Pharmacia Biotech) equilibrated with 50 mM Tris-HCl (pH 8.0) containing 100 mM NaCl and 0.1 mM EDTA and eluted with the same buffer. As a result, RNase HII was eluted at a position corresponding to a molecular weight of 17 kilodalton. This molecular weight corresponds to that of RNase HII in a form of a monomer.

The eluted RNase HII was used as a Pfu RNase HII preparation. An RNase H activity was measured using the thus obtained Pfu RNase HII preparation as follows.

10 mM Tris-HCl (pH 8.0), 1 mM dithiothreitol (Nacalai Tesque), 0.003% bovine serum albumin (fraction V, Sigma), 4% glycerol, 20 μg/ml poly(dT) (Amersham Pharmacia Biotech) and 30 μg/ml poly(rA) (Amersham Pharmacia Biotech) were mixed together. The mixture was incubated at 37° C. for 10 minutes and used as a substrate solution for measuring an RNase H activity.

1 μl of 1 M $MnCl_2$ was added to 100 μl of the substrate solution. The mixture was incubated at 40° C. An appropriate dilution of the Pfu RNase HII preparation was added to the mixture to initiate a reaction. After reacting at 40° C. for 30 minutes, 10 μl of 0.5 M EDTA was added thereto to terminate the reaction. Absorbance at 260 nm was then measured.

As a result, the value of absorbance at 260 nm for a reaction mixture in which the Pfu RNase HII preparation was added was higher than that for a reaction mixture in which 10 μl of 0.5 M EDTA was added before the addition of the Pfu RNase HII preparation. Thus, it was demonstrated that the preparation had an RNase H activity.

(5) Measurement of Activity of Purified RNase H (a) Preparation of Reagent Solutions Used Reaction mixture for determining activity: The following substances at the indicated final concentrations were contained in sterile water: 40 mM Tris-HCl (pH 7.7 at 37° C.), 4 mM magnesium chloride, 1 mM DTT, 0.003% BSA, 4% glycerol and 24 μM poly(dT).

Poly[8-$^3$H]adenylic acid solution: 370 kBq of a poly[8-$^3$H]adenylic acid solution was dissolved in 200 μl of sterile water.

Polyadenylic acid solution: Polyadenylic acid was diluted to a concentration of 3 mM with sterile ultrapure water.

Enzyme dilution solution: The following substances at the indicated final concentrations were contained in sterile water: 25 mM Tris-HCl (pH 7.5 at 37° C.), 5 mM 2-mercaptoethanol, 0.5 mM EDTA (pH 7.5 at 37° C.), 30 mM sodium chloride and 50% glycerol.

Preparation of heat-denatured calf thymus DNA: 200 mg of calf thymus DNA was suspended and allowed to swell in 100 ml of TE buffer. The solution was diluted to a concentration of 1 mg/ml with sterile ultrapure water based on the absorbance measured at UV 260 nm. The diluted solution was heated at 100° C. for 10 minutes and then rapidly cooled in an ice bath.

(b) Method for Measuring Activity

7 μl of the poly[8-$^3$H]adenylic acid solution was added to 985 μl of the reaction mixture for determining activity prepared in (a) above. The mixture was incubated at 37° C. for 10 minutes. 8 μl of polyadenylic acid was added to the mixture to make the final concentration to 24 μM. The mixture was further incubated at 37° C. for 5 minutes. Thus, 1000 µl of a poly[8-³H]rA-poly-dT reaction mixture was prepared. 200 µl of the reaction mixture was then incubated at 30° C. for 5 minutes. 1 µl of an appropriate serial dilution of an enzyme solution was added thereto. 50 µl each of samples was taken from the reaction mixture over time for use in subsequent measurement. The period of time in minutes from the addition of the enzyme to the sampling is defined as Y. 50 µl of a reaction mixture for total CPM or for blank was prepared by adding 1 µl of the enzyme dilution solution in place of an enzyme solution. 100 µl of 100 mM sodium pyrophosphate, 50 µl of the heat-denatured calf thymus DNA solution and 300 µl of 10% trichloroacetic acid (300 µl of ultrapure water for measuring total CPM) were added to the sample. The mixture was incubated at 0° C. for 5 minutes, and then centrifuged at 10000 rpm for 10 minutes. After centrifugation, 250 µl of the resulting supernatant was placed in a vial. 10 ml of Aquasol-2 (NEN Life Science Products) was added thereto. CPM was measured in a liquid scintillation counter.

(c) Calculation of Units

Unit value for each enzyme was calculated according to the following equation.

Unit/ml={(measured $CPM$–blank $CPM$)×1.2*×20× 1000×dilution rate}200 (µl)/(total $CPM$×Y (min.)×50 (µl)×9**)

1.2*: Amount in nmol of poly[8-³H]rA-poly-dT contained in total CPM per 50 µl.

9**: Correction coefficient.

Referential Example 2

Cloning of RNase HII Gene from *Archaeoglobus fulgidus*

(1) Preparation of Genomic DNA from *Archaeoglobus fulgidus*

Cells of *Archaeoglobus fulgidus* (purchased from Deutsche Sammlung von Mikroorganismen und Zellkulturen GmbH; DSM4139) collected from 8 ml of a culture was suspended in 100 µl of 25% sucrose, 50 mM Tris-HCl (pH 8.0). 20 µl of 0.5 M EDTA and 10 µl of a 10 mg/ml lysozyme chloride (Nacalai Tesque) aqueous solution was added thereto. The mixture was reacted at 20° C. for 1 hour. After reaction, 800 µl of a mixture containing 150 mM NaCl, 1 mM EDTA and 20 mM Tris-HCl (pH 8.0), 10 µl of 20 mg/ml proteinase K (Takara Shuzo) and 50 µl of a 10% sodium lauryl sulfate aqueous solution were added to the reaction mixture. The mixture was incubated at 37° C. for 1 hour. After reaction, the mixture was subjected to phenol-chloroform extraction, ethanol precipitation and air-drying, and then dissolved in 50 µl of TE to obtain a genomic DNA solution.

(2) Cloning of RNase HII Gene

The entire genomic sequence of the *Archaeoglobus fulgidus* has been published [Klenk, H. P. et al., Nature, 390: 364–370 (1997)]. The existence of one gene encoding a homologue of RNase HII (AF0621) was known (SEQ ID NO:13, http://www.tigr.org/tdb/CMR/btm/htmls/SplashPage.htlm).

Primers AfuNde (SEQ ID NO:14) and AfuBam (SEQ ID NO:15) were synthesized on the basis of the sequence of the AF0621 gene (SEQ ID NO:13).

A PCR was carried out using 30 ng of the *Archaeoglobus fulgidus* genomic DNA prepared in Referential Example 2-(1) as a template, and 20 pmol of AfuNde and 20 pmol of AfuBam as primers in a volume of 100 µl. Pyrobest DNA polymerase (Takara Shuzo) was used as a DNA polymerase for the PCR according to the attached protocol. The PCR was carried out as follows: 40 cycles of 94° C. for 30 seconds, 55° C. for 30 seconds and 72° C. for 1 minute. An amplified DNA fragment of about 0.6 kb was digested with NdeI and BamHI (both from Takara Shuzo). The resulting DNA fragment was inserted between the NdeI site and the BamHI site in a plasmid vector pTV119Nd (a plasmid in which the NcoI site in pTV119N is converted into a NdeI site) to make a plasmid pAFU204.

(3) Determination of Base Sequence of DNA Fragment Containing RNase HII Gene

The base sequence of the DNA fragment inserted into pAFU204 obtained in Referential Example 2-(2) was determined according to a dideoxy method.

Analysis of the determined base sequence revealed an open reading frame presumably encoding RNase HII. The base sequence of the open reading frame is shown in SEQ ID NO:16. The amino acid sequence of RNase HII deduced from the base sequence is shown in SEQ ID NO:17.

*Escherichia coli* JM109 transformed with the plasmid pAFU204 is designated and indicated as *Escherichia coli* JM109/pAFU204, and deposited on Feb. 22, 2001 at International Patent Organism Depositary, National Institute of Advanced Industrial Science and Technology, AIST Tsukuba Central 6, 1-1, Higashi 1-Chome, Tsukuba-shi, Ibaraki-ken 305-8566, Japan under accession number FERM P-18221 and at International Patent Organism Depositary, National Institute of Advanced Industrial Science and Technology under accession number FERM BP-7691 (date of transmission to international depositary authority: Aug. 2, 2001).

(4) Preparation of Purified RNase HII Preparation

*Escherichia coli* JM109 was transformed with pAFU204 obtained in Referential Example 2-(2). The resulting *Escherichia coli* JM109 harboring pAFU204 was inoculated into 2 L of LB medium containing 100 µg/ml of ampicillin and cultured with shaking at 37° C. for 16 hours. After cultivation, cells collected by centrifugation were suspended in 37.1 ml of a sonication buffer [50 mM-Tris-HCl (pH 8.0), 1 mM EDTA, 2 mM phenylmethanesulfonyl fluoride] and sonicated. A supernatant obtained by centrifuging the sonicated suspension at 12000 rpm for 10 minutes was heated at 70° C. for 15 minutes. It was then centrifuged at 12000 rpm for 10 minutes again to collect a supernatant. Thus, 40.3 ml of a heated supernatant was obtained.

The heated supernatant was subjected to RESOURSE Q column (Amersham Pharmacia Biotech) equilibrated with Buffer A [50 mM Tris-HCl (pH 8.0), 1 mM EDTA] and chromatographed using FPLC system (Amersham Pharmacia Biotech). As a result, RNase HII flowed through the RESOURSE Q column.

The flow-through RNase HII fraction was subjected to RESOURSE S column (Amersham Pharmacia Biotech) equilibrated with Buffer A and chromatographed using FPLC system (Amersham Pharmacia Biotech). As a result, RNase HII flowed through the RESOURSE S column.

40.0 ml of the flow-through RNase HII fraction was subjected to three rounds of dialysis against 2 L of Buffer B (50 mM Tris-HCl (pH 7.0), 1 mM EDTA) containing 50 mM NaCl for 2 hours. 40.2 ml of the dialyzed enzyme solution was subjected to HiTrap-heparin column (Amersham Pharmacia Biotech) equilibrated with Buffer B containing 50 mM NaCl and eluted with a linear gradient of 50 to 550 mM NaCl using FPLC system. As a result, a fraction containing RNase HII eluted with about 240 mM NaCl was obtained.

7.8 ml of the RNase HII fraction was concentrated by ultrafiltration using Centricon-10 (Amicon). Four portions separated from about 600 μl of the concentrate were subjected to Superose 6 gel filtration column (Amersham Pharmacia Biotech) equilibrated with 50 mM Tris-HCl (pH 7.0) containing 100 mM NaCl and 0.1 mM EDTA and eluted with the same buffer. As a result, RNase HII was eluted at a position corresponding to a molecular weight of 30.0 kilodalton. This molecular weight corresponds to that of RNase HII in a form of a monomer.

The RNase HII eluted as described above was used as an Afu RNase HII preparation.

An enzymatic activity was measured as described in Referential Example 1-(5) using the thus obtained Afu RNase HII preparation. As a result, an RNase H activity was observed for the Afu RNase HII preparation.

Unit value of a heat-resistant RNase H in the following Examples was calculated as follows.

1 mg of poly(rA) or poly(dT) (both from Amersham Pharmacia Biotech) was dissolved in 1 ml of 40 mM Tris-HCl (pH 7.7) containing 1 mM EDTA to prepare a poly(rA) solution and a poly(dT) solution.

The poly(rA) solution (to a final concentration of 20 μg/ml) and the poly(dT) solution (to a final concentration of 30 μg/ml) were then added to 40 mM Tris-HCl (pH 7.7) containing 4 mM MgCl$_2$, 1 mM DTT, 0.003% BSA and 4% glycerol. The mixture was reacted at 37° C. for 10 minutes and then cooled to 4° C. to prepare a poly(rA)-poly(dT) solution. 1 μl of an appropriately diluted enzyme solution was added to 100 μl of the poly(rA)-poly(dT) solution. The mixture was reacted at 40° C. for 10 minutes. 10 μl of 0.5 M EDTA was added thereto to terminate the reaction. Absorbance at 260 nm was then measured. As a control, 10 μl of 0.5 M EDTA was added to the reaction mixture, the resulting mixture was reacted at 40° C. for 10 minutes, and the absorbance was then measured. A value (difference in absorbance) was obtained by subtracting the absorbance for the control from the absorbance for the reaction in the absence of EDTA. Thus, the concentration of nucleotide released from poly(rA)-poly(dT) hybrid by the enzymatic reaction was determined on the basis of the difference in absorbance. One unit of an RNase H was defined as an amount of enzyme that increases $A_{260}$ corresponding to release of 1 nmol of ribonucleotide in 10 minutes, which was calculated according to the following equation:

Unit=[Difference in Absorbance×Reaction Volume (ml)]/0.0152×(110/100)×Dilution Rate Example 1

Detection of Base Substitution in Human c-Ki-ras Gene (1) Preparation of Template DNA fragments each having a sequence GGT (Gly), CGT (Arg), TGT (Cys) or AGT (Ser) for codon 12 in human c-Ki-ras exon 1 were prepared. Briefly, amplification products obtained by PCRs using template DNAs corresponding to the above-mentioned codons in ras Mutant Set c-Ki-ras codon 12 (Takara Shuzo) and ras Gene Primer Set c-Ki-ras/12 (Takara Shuzo) were cloned into a vector pT7-Blue (Novagen). PCRs using the thus obtained recombinant plasmids as templates and M13 primers M4 and RV (both from Takara Shuzo) were carried out. The resulting amplified fragments were recovered and designated as templates 12G, 12R, 12C and 12S, respectively.

(2) Detection of Base Substitution

Three chimeric oligonucleotides having base sequences of SEQ ID NOS:7 to 9 as forward Nucleotides for specifically detecting the template 12G were synthesized on the basis of the base sequence of human c-Ki-ras exon 1. The hydroxyl group at the 3-position of ribose moiety of the nucleotide at the 3' end of each chimeric oligonucleotide was modified with aminohexyl. Each of the Nucleotides had a sequence complementary to the base sequence of human c-Ki-ras exon 1 in which codon 12 encoded Gly. An oligonucleotide having a base sequence of SEQ ID NO:6 was synthesized as an antisense primer for nucleic acid amplification.

Figure 2:
FIG. 2 illustrates results for detection of a base substitution in a human gene according to the method for detecting a base substitution of the present invention.
Figure 2:
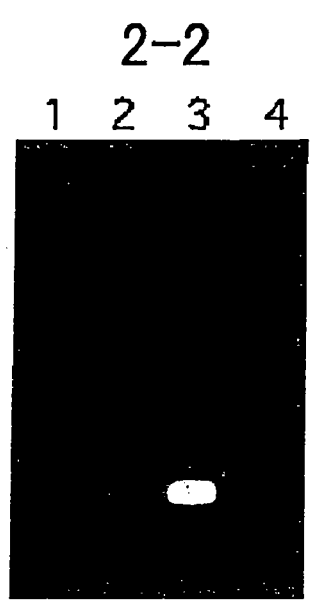
Figure 2:
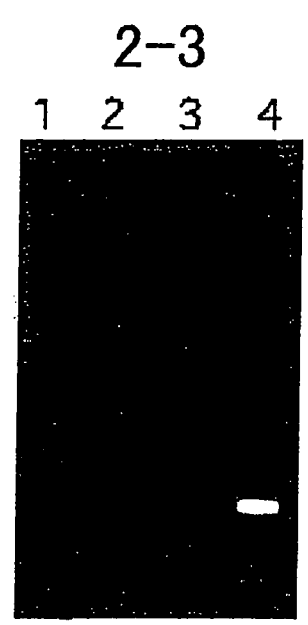
Figure 3:
FIG. 3 illustrates results for detection of a base substitution in a human gene according to the method for detecting a base substitution of the present invention.
Figure 3:

A reaction mixture of a total volume of 5 μl containing 50 pmol each of the forward Nucleotide and the antisense primer, 1 μl of a 0.25% propylenediamine aqueous solution and 1 μg of one of the templates 12G, 12C, 12R and 12S as a template was prepared. The forward Nucleotide and the antisense primer were annealed to the template by heating at 98° C. for 2 minutes and then at 53° C. in Thermal Cycler Personal (Takara Shuzo). 20 μl of a mixture containing 0.625 mM dNTP mix, 40 mM Hepes-KOH buffer (pH 7.8), 125 mM potassium acetate, 5 mM magnesium acetate, 0.0125% bovine serum albumin, 1.25% dimethyl sulfoxide, 16 U of Pfu RNase HII as described in Referential Example 1, 5.5 U of BcaBest DNA polymerase (Takara Shuzo) and sterile water was added to the heated mixture to make the final volume to 25 μl. The reaction mixture was incubated at 53° C. for 1 hour. After reaction, 5 μl each of the reaction mixtures was subjected to electrophoresis on 3.0% agarose gel. The results are shown in FIG. 1. The reaction mixtures in which the templates 12G, 12C, 12R and 12S were used were applied to lanes 1 to 4 in the agarose gels as shown in FIGS. 1-1, 1-2 and 1-3, respectively. FIGS. 1-1, 1-2 and 1-3 show results for the reactions in which the Nucleotides of SEQ ID NOS:7, 8 and 9 were used; respectively.

As shown in FIG. 1, using the Nucleotides of SEQ ID NOS:7–9, amplification products were observed only when the template 12G was used, that is, when the target nucleic acid encoded Gly for codon 12. These results show that a base substitution in a target nucleic acid can be distinguished by using the Nucleotide of the present invention. Furthermore, it was confirmed that specific amplification could be improved by using a Nucleotide containing inosine.

Example 2

Detection of other Alleles for c-Ki-ras Codon 12

Based on the results of Example 1, chimeric oligonucleotides having base sequences of SEQ ID NOS:10 to 12 were synthesized as Nucleotides capable of specifically distinguishing the bases of codon 12 in 12R, 12C and 12S prepared in Example 1-(1). SEQ ID NOS:10, 11 and 12 show base sequences corresponding to alleles in which codon 12 encodes Cys, Arg and Ser, respectively. The hydroxyl group at the 3-position of ribose moiety of the nucleotide at the 3' end of each Nucleotide was modified with aminohexyl. Reactions were carried out using these Nucleotides and the antisense primer of SEQ ID NO:6 under reaction conditions as described in Example 1-(2). After reaction, 5 μl each of the reaction mixtures was subjected to electrophoresis on 3.0% agarose gel. The results are shown in FIG. 2. The reaction mixtures in which the templates 12G, 12C, 12R and 12S were used were applied to lanes 1 to 4 in the agarose gels as shown in FIGS. 2-1, 2-2 and 2-3, respectively. FIGS. 2-1, 2-2 and 2-3 show results for the reactions in which the Nucleotides of SEQ ID NOS:10, 11 and 12 were used, respectively.

As shown in FIG. 2, specific amplification products were observed only when the Nucleotides of SEQ ID NOS:10, 11 and 12 were used in combination with the templates 12C, 12R and 12S, respectively. Thus, the Nucleotides of the present invention could exactly distinguish the bases of interest. Furthermore, it was confirmed that specific amplification could be improved by using an oligonucleotide containing inosine.

Example 3

Allele-specific DNA Amplification of Genomic DNA

Reactions were carried out under conditions as described in (2) above. In the reaction, 150 ng or 30 ng of a human genomic DNA (Clontech) for which it had been confirmed that codon 12 in c-Ki-ras exon 1 encodes Gly (GGT), the Nucleotides of SEQ ID NOS:7, 10, 11 and 12 (corresponding to Gly, Cys, Arg and Ser at codon 12, respectively) which had been demonstrated to be able to specifically detect the four alleles for codon 12 in Example 1 and 2, as well as the antisense primer of SEQ ID NO:6 were used. After reaction, 5 µl each of the reaction mixtures was subjected to electrophoresis on 3.0% agarose gel. The results are shown in FIG. 3.

The reaction mixtures in which the Nucleotide of SEQ ID NOS:7, 10, 11 and 12 were used were applied to lanes 1 to 4 in the agarose gels as shown in FIGS. 3-1 and 3-2, respectively. FIGS. 3-1 and 3-2 show results for the reactions in which 150 ng and 30 ng of the human genomic DNA were used, respectively.

As shown in FIG. 3, amplification of a DNA fragment was observed only when the Nucleotide of SEQ ID NO:7 was used regardless of the amount of the human genomic DNA, whereas amplification of a DNA fragment was not observed using other Nucleotides. These results confirmed that the method for detecting a base substitution of the present invention could be used to detect a specific allele in a genomic DNA.

Example 4

Detection Using Various RNase H's

Use of various RNase H's in the detection of a base substitution as described in Example 1 was examined.

Figure 4:
FIG. 4 illustrates results for detection of a base substitution in a human gene according to the method for detecting a base substitution of the present invention.
Figure 4:
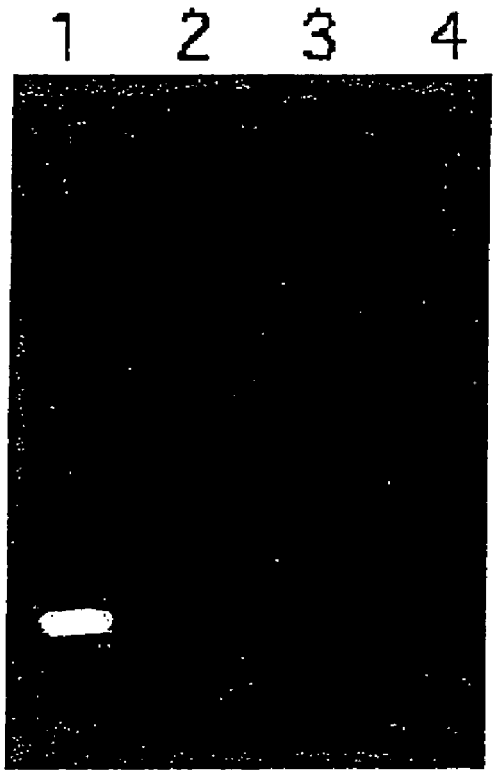

Specifically, Afu RNase HII as described in Referential Example 2 or Mja RNase HII, an RNase H derived from *Methanococcus jannashi*, prepared as described in Structure, 8:897–904 was used in place of Pfu RNase HII. Reactions were carried out under conditions as described in Example 1 using the Nucleotide of SEQ ID NO:7 as a forward Nucleotide and the oligonucleotide of SEQ ID NO:6 as an antisense primer. After reaction, 5 µl each of the reaction mixtures was subjected to electrophoresis on 3.0% agarose gel. The results are shown in FIG. 4. The reaction mixtures in which the templates 12G, 12C, 12R and 12S were used were applied to lanes 1 to 4 in the agarose gels as shown in FIGS. 4-1 and 4-2, respectively. FIGS. 4-1 and 4-2 show results for the reactions in which Afu RNase HII and Mja RNase HII were used, respectively.

As shown in FIG. 4, using Afu RNase HII and Mja RNase HII, amplification products were observed only when the template 12G was used, that is, when the target nucleic acid encoded Gly for codon 12. These results show that a base substitution in a target nucleic acid can be distinguished using these RNase H's.

Example 5

Figure 5:
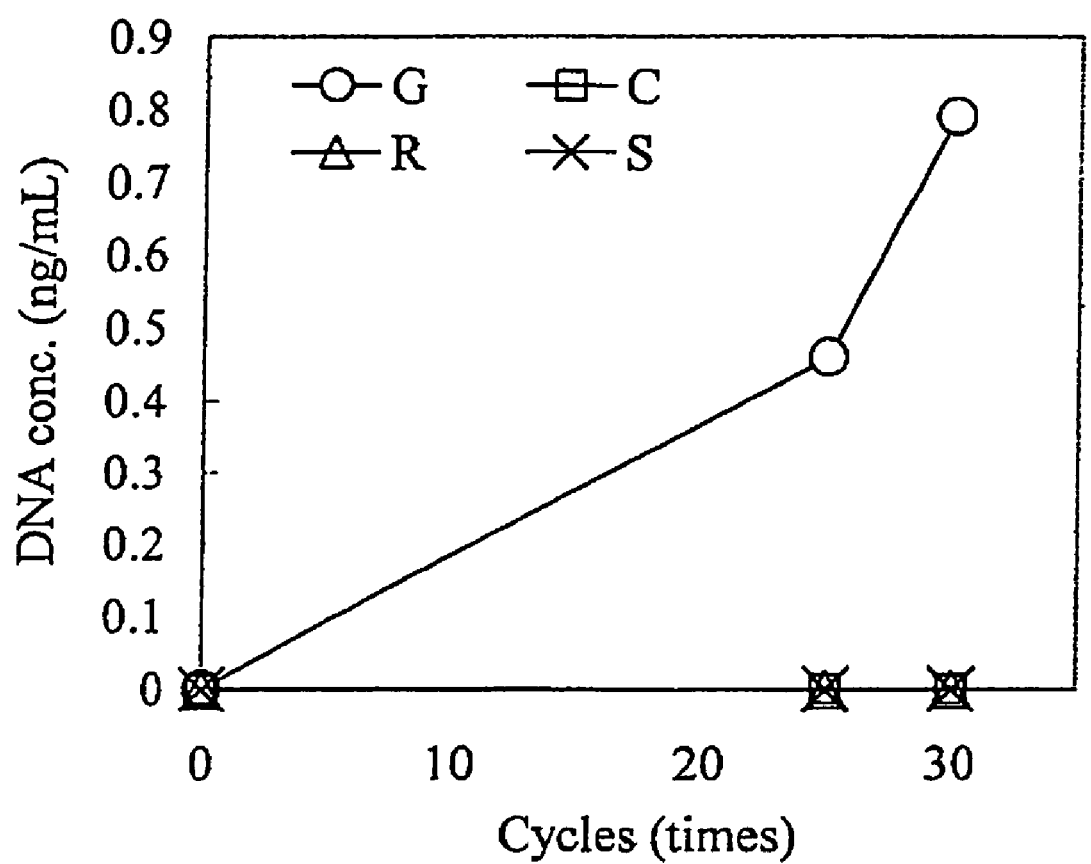
FIG. 5 is a graph that illustrates results for detection of a base substitution in a human gene according to the method for detecting a base substitution of the present invention.

Detection of SNP Using DNA Amplification Reaction System (PCR) that Requires Denaturation Step The method of the present invention was examined using a DNA amplification reaction system that requires a denaturation step. A chimeric oligonucleotide of SEQ ID NO:25 was synthesized as a sense Nucleotide for specifically detecting the template 12G on the basis of the base sequence of human c-Ki-ras exon 1. The hydroxyl group at the 3-position of ribose moiety of the nucleotide at the 3' end of the Nucleotide was modified with aminohexyl. A primer having the base sequence of SEQ ID NO:18 was synthesized as an antisense primer as well. A reaction mixture of total volume of 24 µl containing 50 pmol each of the synthetic Nucleotide and the primer (the sense Nucleotide and the antisense primer), 2.5 µl of Ex Taq buffer (Takara Shuzo), 2 µl of 2.5 mM dNTP mix, 50 U of Afu RNase HII and 0.625 U of Ex Taq DNA polymerase (Takara Shuzo) was prepared. 1 µl of a 10 ng/µl solution of the template 12G, 12C, 12R or 12S prepared in Example 1 was added to the reaction mixture. A PCR was carried out using Thermal Cycler (Takara Shuzo) as follows: 25 or 30 cycles of 94° C. for 5 seconds, 59° C. for 2 minutes and 72° C. for 5 seconds. After reaction, 1 µl each of the reaction mixtures was analyzed using Agilent 2100 Bioanalyzer (Hewlett-Packard). The results are shown in FIG. 5. FIG. 5 is a graph that illustrates the amounts of amplification products of interest for the respective templates. The vertical axis represents the amount of amplification product of interest and the horizontal axis represents the PCR cycle number. As shown in FIG. 5, specific amplification of the DNA of interest was observed only when the template 12G, of which the allele was consistent with the primer used for detection, was used. Thus, it was confirmed that the method of the present invention was also effective for a DNA amplification reaction system that requires a step of denaturing a nucleic acid as a template.

Example 6

Allele-specific Detection of K-ras Codon 61

Figure 6:
FIG. 6 illustrates results for detection of a base substitution in a human gene according to the method for detecting a base substitution of the present invention.
Figure 6:
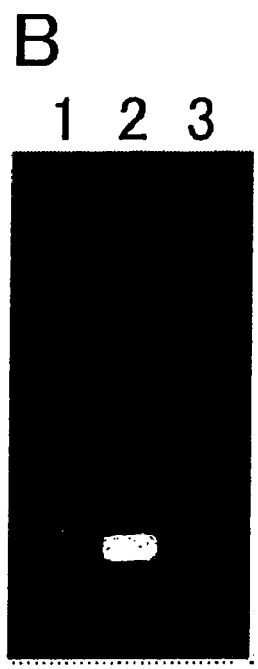
Figure 6:

Detection of another base substitution was examined. Specifically, DNA fragments each having a sequence CAA (Glu), AAA (Lys) or GAA (Gln) for codon 61 in human c-Ki-ras exon 2 amplified by PCRs using the DNA primers of SEQ ID NOS:19 and 20 were cloned into the vector pT7-Blue. The vectors into which the DNA fragments were cloned were purified according to a conventional method and designated as 61Q, 61K and 61E, respectively. Based on the results of Example 1-(2), chimeric oligonucleotides of SEQ ID NOS:21, 22 and 23 were synthesized as Nucleotides for specifically detecting the respective vectors 61Q, 61K and 61E on the basis of the base sequence of human c-Ki-ras exon 2. The hydroxyl group at the 3-position of ribose moiety of the nucleotide at the 3' end of each Nucleotide was modified with aminohexyl. The following reaction was carried out using the Nucleotide as a sense primer and the primer of SEQ ID NO:24 as an antisense primer. A reaction mixture of a total volume of 5 µl containing 50 pmol each of the synthetic oligonucleotide primers (sense and antisense primers), 1 µl of a 0.05% propylenediamine aqueous solution and 10 pg of one of the template DNAs 61Q, 61K and 61E was prepared. The primers were annealed to the template by heating at 98° C. for 2 minutes and then at 53° C. in Thermal Cycler Personal (Takara Shuzo). 20 µl of a mixture containing 0.625 mM dNTP mix; 40 mM Hepes-KOH buffer (pH 7.8), 125 mM potassium acetate, 5 mM magnesium acetate, 0.0125% bovine serum albumin, 1.25% dimethyl sulfoxide, 11 U of Afu RNase HII (Takara Shuzo), 5.5 U of BcaBest DNA polymerase (Takara Shuzo) and sterile water was added to the heated mixture to make the final volume to 25 µl. The reaction mixture was incubated at 58° C. for 1 hour. After reaction, 5 µl each of the reaction mixtures was subjected to electrophoresis on 3.0% agarose gel. The results are shown in FIG. 6. FIG. 6A is an electrophoresis pattern that represents results for detection using the primer of SEQ ID NO:21 for detecting 61Q. Lanes 1, 2 and 3 represent results obtained using the templates 61Q, 61K and 61E as templates, respectively. FIG. 6B is an electrophoresis pattern that represents results for detection using the primer of SEQ ID NO:22 for detecting 61K. Lanes 1, 2 and 3 represent results obtained using the templates 61Q, 61K and 61E, respectively. FIG. 6C is an electrophoresis pattern that represents results for detection obtained using the primer of SEQ ID NO:23 for detecting 61E. Lanes 1, 2 and 3 represent results obtained using the templates 61Q, 61K and 61E, respectively.

As shown in FIGS. 6A, 6B and 6C, it was confirmed that the DNA amplification products of interest were obtained by ICAN reactions in an allele-specific manner using SEQ ID NOS:21, 22 and 23. Thus, it was confirmed that the method of the present invention was effective if the objective base substitution was changed.

Example 7

Allele-specific Detection of CYP2C19(636)

(1) A detection method for distinguishing genetic homo-type from hetero-type was examined. The allele for the 636th base in human CYP2C19 was selected as a subject. First, DNA fragments in which the 636 th base in human CYP2C19 was G or A amplified by PCRs using DNA primers of SEQ ID NOS:26 and 27 were cloned into the vector pT7-Blue. The plasmids into which these DNA fragments were cloned were purified according to a conventional method and designated as plasmids 636G and 636A.

Figure 7:
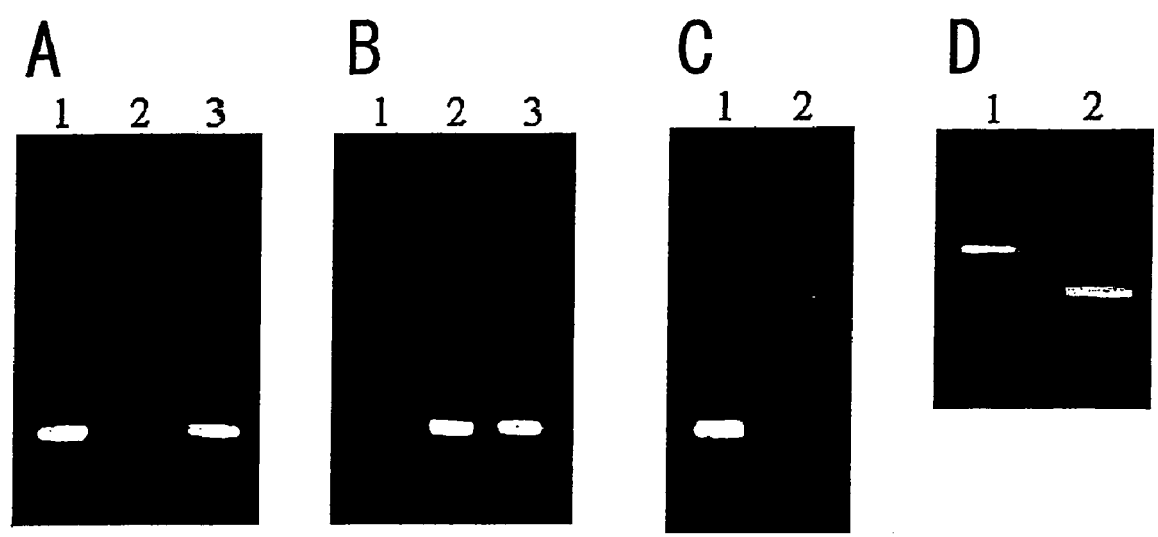
FIG. 7 illustrates results for detection of a base substitution in a human gene according to the method for detecting a base substitution of the present invention.

The plasmids 636G and 636A as well as a plasmid 636G/A prepared by mixing the plasmids 636G and 636A at 1:1 were used as templates. The plasmids 636G and 636A served as models for genetic homo-type, whereas the plasmid 636G/A served as a model for genetic hetero-type. Next, Nucleotide of SEQ ID NOS:28 and 29 were synthesized as Nucleotides for specifically detecting the 636G and the 636A, respectively. The following reaction was carried out using the Nucleotide as a sense primer and the primer of SEQ ID NO:30 as an antisense primer. A reaction mixture of a total volume of 5 µl containing 50 pmol each of the synthetic oligonucleotide primers (sense and antisense primers), 1 µl of a 0.05% propylenediamine aqueous solution and 1 pg of one of the plasmids 636G, 636A and 636G/A as a template DNA was prepared. The primers were annealed to the template by heating at 98° C. for 2 minutes and then at 53° C. in Thermal Cycler Personal (Takara Shuzo). 20 µl of a mixture containing 0.625 mM dNTP mix, 40 mM Hepes-KOH buffer (pH 7.8), 125 mM potassium acetate, 5 mM magnesium acetate, 0.0125% bovine serum albumin, 1.25% dimethyl sulfoxide, 11 U of Afu RNase HII, 5.5 U of BcaBest DNA polymerase and sterile water was added to the heated mixture to make the final volume to 25 µl. The reaction mixture was incubated at 53° C. for 1 hour. After reaction, 5 µl each of the reaction mixtures was subjected to electrophoresis on 3.0% agarose gel. The results are shown in FIGS. 7A and 7B. FIG. 7A is an electrophoresis pattern that represents results for detection using the Nucleotide 636G. Lanes 1, 2 and 3 represent results obtained using the plasmids 636G, 636A and 636G/A as templates, respectively.

FIG. 7B is an electrophoresis pattern that represents results for detection using the Nucleotide 636A. Lanes 1, 2 and 3 represent results obtained using the plasmids 636G, 636A and 636G/A as templates, respectively. As shown in FIGS. 7A and 7B, it was confirmed that detection could be carried out in an allele-specific manner using the Nucleotides.

(2) A human genomic DNA was used as a template in comparison with PCR-RFLP for analysis. SNP typing was carried out as described in (1) above using 150 ng of a human genomic DNA (Clontech) as a template. The results are shown in FIG. 7C. FIG. 7C is a electrophoresis pattern that represents results for SNP typing of the human genomic DNA. Lanes 1 and 2 and represent results obtained using the Nucleotides 636G and 636A, respectively.

As shown in FIG. 7C, the amplified DNA of interest was detected only when the Nucleotide 636G was used. The allele for the 636th base in CYP2C19 of the genomic DNA was determined to be homo-type (636G/G).

On the other hand, typing was carried out by PCR-RFLP using the human genomic DNA. A PCR was carried out using 150 ng of the genomic DNA and primers of SEQ ID NOS:26 and 27. The resulting PCR amplification product was treated with BamHI and the reaction mixture was subjected to electrophoresis on 3.0% agarose gel. The results are shown in FIG. 7D. FIG. 7D is an electrophoresis pattern that represents results for typing by PCR-RFLP using the human genomic DNA as a template. Lanes 1 and 2 represent results for the PCR amplification product and the PCR amplification product digested with BamHI, respectively.

As shown in FIG. 7D, the PCR amplification product was completely digested with BamHI. Thus, the allele for the 636th base in CYP2C19 in the genomic DNA was also determined to be homo-type (636G/G) by PCR-RFLP. It was confirmed that the results obtained using the method for detecting a base substitution of the present invention were consistent with those obtained using the conventional SNP typing by PCR-RFLP.

(3) Using the plasmids 636G, 636A, 636G/A prepared in (1) above, a detection method was examined assuming genotype of a homologous chromosome. The reaction was carried out as follows. First, the Nucleotides 636G and 636A having fluorescence labels Rox (ABI) and Fam (ABI) being attached at the 5'-termini which are distinguishable each other were synthesized. A mixture containing equal amounts of the fluorescence labeled Nucleotides was used. Detection was carried out as described in (1) above. After reaction, a portion of each reaction mixture was subjected to electrophoresis on 3.0% agarose gel to fully separate the amplification product from the unreacted fluorescence labeled Nucleotide. After electrophoresis, the agarose gel was analyzed using FM-BIO II Multi-View (Takara Shuzo). As a result, when the plasmid 636G was used as a template, only the fluorescence signal from the fluorescent label Rox was observed. When the plasmid 636A was used as a template, only the fluorescence signal from the fluorescent label Fam was observed. Furthermore, when the plasmid 636G/A was used as a template, the fluorescence signals from both Rox and Fam were observed. Based on these results, it was confirmed that the method of the present invention was useful as a method that could be used to analyze the genotype (homo-type or hetero-type) on a homologous chromosome.

Example 8

Typing Using Genomic DNA Extracted from Whole Blood

Figure 8:
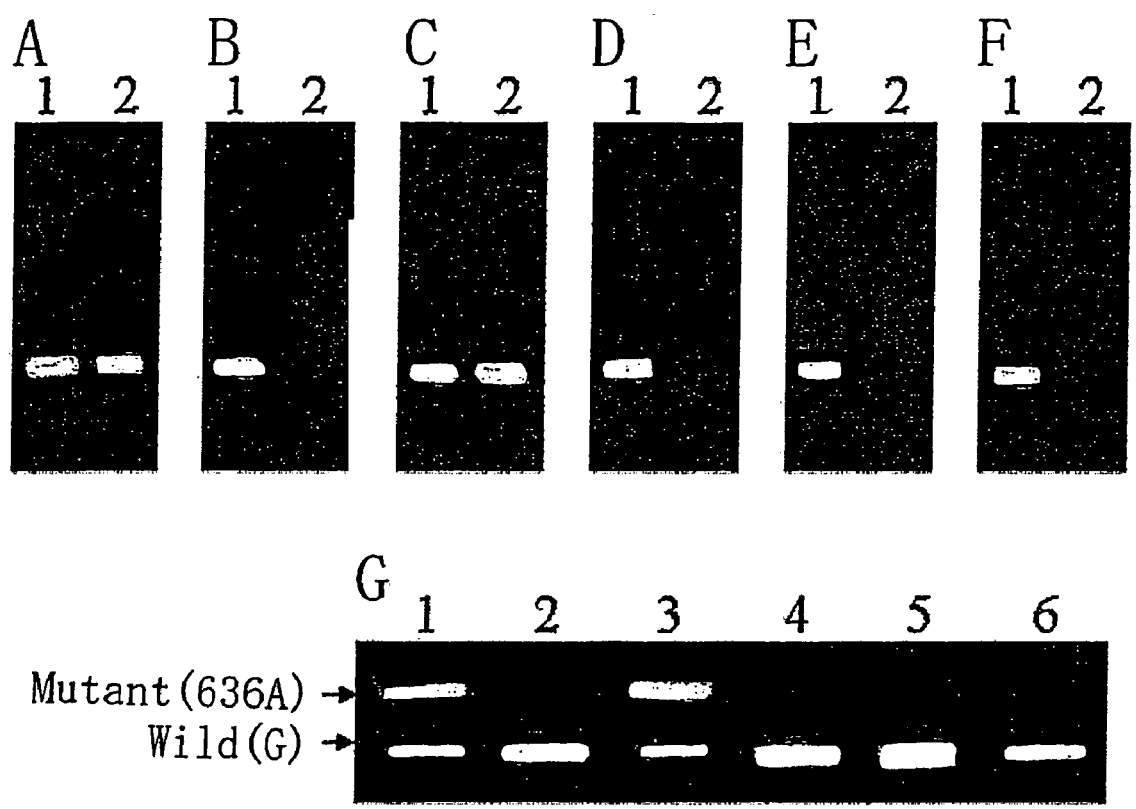
FIG. 8 illustrates results for detection of a base substitution in a human gene according to the method for detecting a base substitution of the present invention.

A genomic DNA was prepared using Dr. GenTLE™ (Takara Shuzo) from 200 μl each of whole blood samples 1–6 collected from healthy individuals after obtaining informed consent. SNP typing was carried out as described in Example 7-(1) using 160 ng of the prepared genomic DNA as a template as well as the Nucleotides of SEQ ID NOS:28 and 29 as primers for specifically detecting the alleles 636G and 636A. The results are shown in FIGS. 8A–F. FIGS. 8A–F are electrophoresis patterns that represent results for typings carried out as described in Example 7-(1) using genomic DNAs extracted from the blood samples 1–6 as templates. Lanes 1 and 2 represent results obtained using the Nucleotides of SEQ ID NO:28 (for detecting 636G) and SEQ ID NO:29 (for detecting 636A), respectively. Based on the patterns of amplification products as shown in FIGS. 8A–F, the alleles of the respective blood samples for the 636th base in CYP2C19 were typed as follows (1: G/A, 2: G/G, 3: G/A, 4: G/G, 5: G/G, 6: G/G). On the other hand, typing by PCR-RFLP was carried out as described in Example 7-(2) using the same genomic DNA as a template. The results are shown in FIG. 8G. FIG. 8G is an electrophoresis pattern that represents results for typing by PCR-RFLP using genomic DNAs prepared from the blood samples 1–6 as templates. Lanes 1–6 represent results obtained using the genomic DNAs extracted from the blood samples 1–6 as templates, respectively. Based on the results of electrophoresis as shown in FIG. 8G which shows the cleavage pattern of the PCR amplification products obtained using the DNAs prepared from the respective blood samples as templates, the alleles for the 636th base in CYP2C19 were typed as follows (1: G/A, 2: G/G, 3: G/A, 4: G/G, 5: G/G, 6: G/G), which were consistent with those as described above.

As described above, it was confirmed that the method of the present invention was also effective when a practical clinical test sample was used.

Industrial Applicability

The Nucleotide of the present invention and the method for detecting a base substitution using said Nucleotide as described above are useful for detecting a naturally occurring or artificially introduced base substitution.

According to the present invention, the presence of a base substitution in a target nucleic acid can be detected conveniently with reproducibility. The method of the present invention can be readily combined with a known nucleic acid amplification method, and can be used to detect a base substitution with high sensitivity. Furthermore, by using Nucleotides having appropriate sequences in combination, it is possible to have information about the presence of a base substitution and the type of the substituted base at the same time.

The present invention can be used for detecting or identifying a base substitution (e.g., SNP) generated in a genomic DNA of an organism such as a polymorphism or a variation. Thus, the present invention is useful in fields of genomic drug development and genomic medicine for searching for a disease gene in humans, analysis of drug resistance or the like.

Sequence Listing Free Text

SEQ ID NO:1: a gene encoding a polypeptide having a RNaseHII activity from *Pyrococcus horikoshii*

SEQ ID NO:2: PCR primer 1650Nde for cloning a gene encoding a polypeptide having a RNase HII activity from *Pyrococcus furiosus*

SEQ ID NO:3: PCR primer 1650Bam for cloning a gene encoding a polypeptide having a RNaseHII activity from *Pyrococcus furiosus*

SEQ ID NO:6: Chimeric oligonucleotide primer to amplify the DNA of a portion of human c-Ki-ras gene. "nucleotides 18 to 20 are ribonucleotides-other nucleotides are deoxyribonucleotides"

SEQ ID NO:7: Chimeric oligonucleotide to detect the nucleotide substitution on human c-Ki-ras gene. "nucleotides 13 to 15 are ribonucleotides-other nucleotides are deoxyribonucleotides and the 3'-OH group of the nucleotide at 3' end is protected with amino hexyl group"

SEQ ID NO:8: Chimeric oligonucleotide primer precursor to detect the nucleotide substitution on human c-Ki-ras gene. "nucleotides 12 to 15 are ribonucleotides, nucleotide 17 is inosine-other nucleotides are deoxyribonucleotides and the 3'-OH-group of the nucleotide at 3' end is protected with amino hexyl group"

SEQ ID NO:9: Chimeric oligonucleotide to detect the nucleotide substitution on human c-Ki-ras gene. "nucleotides 14 and 15 are ribonucleotides-other nucleotides are deoxyribonucleotides and the 3'-OH group of the nucleotide at 3' end is protected with amino hexyl group"

SEQ ID NO:10: Chimeric oligonucleotide to detect the nucleotide substitution on human c-Ki-ras gene. "nucleotides 13 to 15 are ribonucleotides-other nucleotides are deoxyribonucleotides and the 3'-OH group of the nucleotide at 3' end is protected with amino hexyl group"

SEQ ID NO:11: Chimeric oligonucleotide to detect the nucleotide substitution on human c-Ki-ras gene. "nucleotides 13 to 15 are ribonucleotides-other nucleotides are deoxyribonucleotides and the 3'-OH group of the nucleotide at 3' end is protected with amino hexyl group"

SEQ ID NO:12: Chimeric oligonucleotide to detect the nucleotide substitution on human c-Ki-ras gene. "nucleotides 13 to 15 are ribonucleotides, nucleotide 17 is inosine-other nucleotides are deoxyribonucleotides and the 3'-OH group of the nucleotide at 3' end is protected with amino hexyl group"

SEQ ID NO:13: Base sequence of AF0621 gene from *Archaeoglobus fulgidus*.

SEQ ID NO:14: PCR primer AfuNde for cloning a gene encoding a polypeptide having a RNaseHII activity from *Archaeoglobus fulgidus*.

SEQ ID NO:15: PCR primer AfuBam for cloning a gene encoding a polypeptide having a RNaseHII activity from *Archaeoglobus fulgidus*.

SEQ ID NO:16: Base sequence of ORF in RnaseHII from *Archaeoglobus fulgidus*.

SEQ ID NO:17: Amino acid sequence of RNaseHII from *Archaeoglobus fulgidus*.

SEQ ID NO:18: Designed PCR primer to amplify a portion of c-ki-ras oncogene exon 1

SEQ ID NO:19 Designed PCR primer to amplify a portion of human c-ki-ras oncogene exon 2

SEQ ID NO:20: Designed PCR primer to amplify a portion of human c-ki-ras oncogene exon 2

SEQ ID NO:21: Chimeric oligonucleotide to detect the nucleotide substitution on human c-Ki-ras gene. "nucleotides 13 to 15 are ribonucleotides-other nucleotides are deoxyribonucleotides and the 3'-OH group of the nucleotide at 3' end is protected with amino hexyl group"

SEQ ID NO:22: Chimeric oligonucleotide to detect the nucleotide substitution on human c-Ki-ras gene. "nucleotides 13 to 15 are ribonucleotides-other nucleotides are deoxyribonucleotides and the 3'-OH group of the nucleotide at 3' end is protected with amino hexyl group"

SEQ ID NO:23: Chimeric oligonucleotide to detect the nucleotide substitution on human c-Ki-ras gene. "nucleotides 13 to 15 are ribonucleotides-other nucleotides are deoxyribonucleotides and the 3'-OH group of the nucleotide at 3' end is protected with amino hexyl group"

SEQ ID NO:24: Chimeric oligonucleotide to detect the nucleotide substitution on human c-Ki-ras gene. "nucleotides 17 to 19 are ribonucleotides-other nucleotides are deoxyribonucleotides"

SEQ ID NO:25: Chimeric oligonucleotide to detect the nucleotide substitution on human c-Ki-ras gene. "nucleotides 16 to 18 are ribonucleotides-other nucleotides are deoxyribonucleotides and the 3'-OH group of the nucleotide at 3' end is protected with amino hexyl group"

SEQ ID NO:26: Designed PCR primer to amplify a portion of human CYP2C19 gene

SEQ ID NO:27: Designed PCR primer to amplify a portion of human CYP2C19 gene

SEQ ID NO:28: Chimeric oligonucleotide to detect the nucleotide substitution on human CYP2C19 gene. "nucleotides 13 to 15 are ribonucleotides-other nucleotides are deoxyribonucleotides and the 3'-OH group of the nucleotide at 3' end is protected with amino hexyl group"

SEQ ID NO:29: Chimeric oligonucleotide to detect the nucleotide substitution on human CYP2C19 gene. "nucleotides 13 to 15 are ribonucleotides-other nucleotides are deoxyribonucleotides and the 3'-OH group of the nucleotide at 3' end is protected with amino hexyl group"

SEQ ID NO:30: Chimeric oligonucleotide primer to amplify a portion of human CYP2C19 gene. "nucleotides 19 to 21 are ribonucleotides-other nucleotides are deoxyribonucleotides".

SEQUENCE LISTING

```
<160> NUMBER OF SEQ ID NOS: 30

<210> SEQ ID NO 1
<211> LENGTH: 663
<212> TYPE: DNA
<213> ORGANISM: Pyrococcus horikoshii

<400> SEQUENCE: 1
atgaaggttg ctggagttga tgaagcgggg aggggccgg  taattggccc gttagtaatt      60
ggagtagccg ttatagatga gaaaaatatt gagaggttac gtgacattgg ggttaaagac     120
tccaaacaat taactcctgg gcaacgtgaa aaactattta gcaaattaat agatatccta     180
gacgattatt atgttcttct cgttaccccc aaggaaatag atgagaggca tcattctatg     240
aatgaactag aagctgagaa attcgttgta gccttgaatt ctttaaggat caagccgcag     300
aagatatatg tggactctgc cgatgtagat cctaagaggt ttgctagtct aataaaggct     360
gggttgaaat atgaagccac ggttatcgcc gagcataaag ccgatgcaaa gtatgagata     420
gtatcggcag catcaataat tgcaaaggtc actagggata gagagataga gaagctaaag     480
caaaagtatg gggaatttgg ttctggctat ccgagtgatc cgagaactaa ggagtggctt     540
gaagaatatt acaaacaata tggtgacttt cctccaatag ttaggagaac ttgggaaacc     600
gctaggaaga tagaggaaag gtttagaaaa aatcagctaa cgcttgataa attccttaag     660
tga                                                                   663

<210> SEQ ID NO 2
<211> LENGTH: 33
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: PCR primer 1650Nde for cloning a gene encoding
      a polypeptide having a RNaseHII activity from Pyrococcus furiosus

<400> SEQUENCE: 2
```

```
caggaggaga gacatatgaa aataggggga att                                       33

<210> SEQ ID NO 3
<211> LENGTH: 33
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: PCR primer 1650Bam for cloning a gene encoding
      a polypeptide having a RNaseHII activity from Pyrococcus furiosus

<400> SEQUENCE: 3
gaaggttgtg gatccacttt ctaaggtttc tta                                      33

<210> SEQ ID NO 4
<211> LENGTH: 672
<212> TYPE: DNA
<213> ORGANISM: Pyrococcus furiosus

<400> SEQUENCE: 4
atgaaaatag ggggaattga cgaagcagga agaggaccag cgatagggcc attagtagta         60
gctactgtcg tcgttgatga gaaaaacatt gagaagctca gaaacattgg agtaaaagac        120
tccaaacaac taacacccca tgaaaggaag aatttatttt cccagataac ctcaatagcg        180
gatgattaca aaatagtgat agtatcccca gaagaaatcg acaatagatc aggaacaatg        240
aacgagttag aggtagagaa gtttgctctc gccttaaatt cgcttcagat aaaaccagct        300
cttatatacg ctgatgcagc ggatgtagat gccaatagat ttgcaagctt gatagagaga        360
agactcaatt ataaggcgaa gattattgcc gaacacaagg ccgatgcaaa gtatccagta        420
gtttcagcag cttcaatact tgcaaaggtt gttagggatg aggaaattga aaaattaaaa        480
aagcaatatg gagactttgg ctctgggtat ccaagtgatc caaaaaccaa gaaatggctt        540
gaagagtact acaaaaaaca caactctttc cctccaatag tcagacgaac ctgggaaact        600
gtaagaaaaa tagaggaaag cattaaagcc aaaaaatccc agctaacgct tgataaattc        660
tttaagaaac ct                                                            672

<210> SEQ ID NO 5
<211> LENGTH: 224
<212> TYPE: PRT
<213> ORGANISM: Pyrococcus furiosus

<400> SEQUENCE: 5

Met Lys Ile Gly Gly Ile Asp Glu Ala Gly Arg Gly Pro Ala Ile Gly
1               5                   10                  15

Pro Leu Val Val Ala Thr Val Val Val Asp Glu Lys Asn Ile Glu Lys
            20                  25                  30

Leu Arg Asn Ile Gly Val Lys Asp Ser Lys Gln Leu Thr Pro His Glu
        35                  40                  45

Arg Lys Asn Leu Phe Ser Gln Ile Thr Ser Ile Ala Asp Asp Tyr Lys
    50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110
```

```
Arg Phe Ala Ser Leu Ile Glu Arg Arg Leu Asn Tyr Lys Ala Lys Ile
            115                 120                 125

Ile Ala Glu His Lys Ala Asp Ala Lys Tyr Pro Val Val Ser Ala Ala
        130                 135                 140

Ser Ile Leu Ala Lys Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Lys Pro
        210                 215                 220
```

<210> SEQ ID NO 6
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide primer to amplify the
      DNA of a portion of human c-Ki-ras gene.
<220> FEATURE:
<221> NAME/KEY: misc_feature
<222> LOCATION: (18)..(20)
<223> OTHER INFORMATION: nucleotides 18 to 20 are ribonucleotides-other
      nucleotides are deoxyribonucleotides

<400> SEQUENCE: 6
ctattgttgg atcatatucg                                              20

<210> SEQ ID NO 7
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (13)..(15)
<223> OTHER INFORMATION: nucleotides 13 to 15 are ribonucleotides-other
      nucleotides are deoxyribonucleotides and the 3'-OH group of the
      nucleotide at 3'end is protected with amino hexyl group.

<400> SEQUENCE: 7
tggtagttgg agcuggtg                                                18

<210> SEQ ID NO 8
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (12)..(15)

```
<223> OTHER INFORMATION: nucleotides 12 to 15 are ribonucleotides,
      nucleotide 17 is inosine-other nucleotides are
      deoxyribonucleotides and the 3'-OH group of the nucleotide at
      3'end is protected with amino hexyl group
<220> FEATURE:
<221> NAME/KEY: misc_feature
<222> LOCATION: (17)..(17)
<223> OTHER INFORMATION: n is a, c, g, t or u

<400> SEQUENCE: 8
tggtagttgg agcuggng                                                    18

<210> SEQ ID NO 9
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (14)..(15)
<223> OTHER INFORMATION: nucleotides 14 and 15 are ribonucleotides-other
      nucleotides are deoxyribonucleotides and the 3'-OH group of the
      nucleotide at 3'end is protected with amino hexyl group.

<400> SEQUENCE: 9
tggtagttgg agcuggtg                                                    18

<210> SEQ ID NO 10
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (13)..(15)
<223> OTHER INFORMATION: nucleotides 13 to 15 are ribonucleotides-other
      nucleotides are deoxyribonucleotides and the 3'-OH group of the
      nucleotide at 3'end is protected with amino hexyl group

<400> SEQUENCE: 10
tggtagttgg agcuugtg                                                    18

<210> SEQ ID NO 11
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (13)..(15)
<223> OTHER INFORMATION: nucleotides 13 to 15 are ribonucleotides-other
      nucleotides are deoxyribonucleotides and the 3'-OH group of the
      nucleotide at 3'end is protected with amino hexyl group.

<400> SEQUENCE: 11
tggtagttgg agcucgtg                                                    18
```

```
<210> SEQ ID NO 12
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (13)..(15)
<223> OTHER INFORMATION: nucleotides 13 to 15 are ribonucleotides.
<220> FEATURE:
<221> NAME/KEY: misc_feature
<222> LOCATION: (17)..(17)
<223> OTHER INFORMATION: nucleotide 17 is inosine-other nucleotides are
      deoxyribonucleotides and the 3'-OH group of the nucleotide at
      3'end is protected with amino hexyl group

<400> SEQUENCE: 12
tggtagttgg agcuagng                                                 18

<210> SEQ ID NO 13
<211> LENGTH: 626
<212> TYPE: DNA
<213> ORGANISM: Archaeoglobus fulgidus

<400> SEQUENCE: 13
atgaaggcag gcatcgatga ggctggaaag ggctgcgtca tcggcccact ggttgttgca    60
ggagtggctt gcagcgatga ggataggctg agaaagcttg gtgtgaaaga ctccaaaaag   120
ctaagtcagg ggaggagaga ggaactagcc gaggaaataa ggaaaatctg cagaacggag   180
gttttgaaag tttctcccga aaatctcgac gaaaggatgg ctgctaaaac cataaacgag   240
attttgaagg agtgctacgc tgaaataatt ctcaggctga agccggaaat tgcttatgtt   300
gacagtcctg atgtgattcc cgagagactt tcgagggagc ttgaggagat tacggggttg   360
agagttgtgg ccgagcacaa ggcggacgag aagtatcccc tggtagctgc ggcttcaatc   420
atcgcaaagg tggaaaggga gcgggagatt gagaggctga agaaaaaatt cggggatttc   480
ggcagcggct atgcgagcga tccgaggaca agagaagtgc tgaaggagtg gatagcttca   540
ggcagaattc cgagctgcgt gagaatgcgc tggaagacgg tgtcaaatct gaggcagaag   600
acgcttgacg atttctaaac gaaacc                                       626

<210> SEQ ID NO 14
<211> LENGTH: 30
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: PCR primer AfuNde for cloning a gene encoding a
      polypeptide having a RNaseHII activity from Archaeoglobus fulgidus

<400> SEQUENCE: 14
aagctgggtt tcatatgaag gcaggcatcg                                    30

<210> SEQ ID NO 15
<211> LENGTH: 30
<212> TYPE: DNA
<213> ORGANISM: Artificial
<220> FEATURE:
<223> OTHER INFORMATION: synthetic
```

```
<220> FEATURE:
<221> NAME/KEY: misc_feature
<223> OTHER INFORMATION: PCR primer AfuBam for cloning a gene encoding a
      polypeptide having a RNaseHII activity from Archaeoglobus fulgidus

<400> SEQUENCE: 15
tggtaataac ggatccgttt agaaatcgtc                                         30

<210> SEQ ID NO 16
<211> LENGTH: 638
<212> TYPE: DNA
<213> ORGANISM: Archaeoglobus fulgidus

<400> SEQUENCE: 16
catatgaagg caggcatcga tgaggctgga agggctgcg tcatcggccc actggttgtt         60
gcaggagtgg cttgcagcga tgaggatagg ctgagaaagc ttggtgtgaa agactccaaa       120
aagctaagtc aggggaggag agaggaacta gccgaggaaa taaggaaaat ctgcagaacg       180
gaggttttga agtttctcc cgaaaatctc gacgaaagga tggctgctaa aaccataaac       240
gagattttga aggagtgcta cgctgaaata attctcaggc tgaagccgga aattgcttat       300
gttgacagtc ctgatgtgat tcccgagaga ctttcgaggg agcttgagga gattacgggg       360
ttgagagttg tggccgagca caaggcggac gagaagtatc ccctggtagc tgcggcttca       420
atcatcgcaa aggtggaaag ggagcgggag attgagaggc tgaaagaaaa attcggggat       480
ttcggcagcg gctatgcgag cgatccgagg acaagagaag tgctgaagga gtggatagct       540
tcaggcagaa ttccgagctg cgtgagaatg cgctggaaga cggtgtcaaa tctgaggcag       600
aagacgcttg acgatttcta aacggatccc cgggtacc                              638

<210> SEQ ID NO 17
<211> LENGTH: 205
<212> TYPE: PRT
<213> ORGANISM: Archaeoglobus fulgidus

<400> SEQUENCE: 17

Met Lys Ala Gly Ile Asp Glu Ala Gly Lys Gly Cys Val Ile Gly Pro
1               5                   10                  15

Leu Val Val Ala Gly Val Ala Cys Ser Asp Glu Asp Arg Leu Arg Lys
            20                  25                  30

Leu Gly Val Lys Asp Ser Lys Lys Leu Ser Gln Gly Arg Arg Glu Glu
        35                  40                  45

Leu Ala Glu Glu Ile Arg Lys Ile Cys Arg Thr Glu Val Leu Lys Val
    50                  55                  60

Ser Pro Glu Asn Leu Asp Glu Arg Met Ala Ala Lys Thr Ile Asn Glu
65                  70                  75                  80

Ile Leu Lys Glu Cys Tyr Ala Glu Ile Ile Leu Arg Leu Lys Pro Glu
                85                  90                  95

Ile Ala Tyr Val Asp Ser Pro Asp Val Ile Pro Glu Arg Leu Ser Arg
            100                 105                 110

Glu Leu Glu Glu Ile Thr Gly Leu Arg Val Val Ala Glu His Lys Ala
        115                 120                 125

Asp Glu Lys Tyr Pro Leu Val Ala Ala Ala Ser Ile Ile Ala Lys Val
    130                 135                 140

Glu Arg Glu Arg Glu Ile Glu Arg Leu Lys Glu Lys Phe Gly Asp Phe
145                 150                 155                 160

Gly Ser Gly Tyr Ala Ser Asp Pro Arg Thr Arg Glu Val Leu Lys Glu
                165                 170                 175
```

```
Trp Ile Ala Ser Gly Arg Ile Pro Ser Cys Val Arg Met Arg Trp Lys
            180                 185                 190

Thr Val Ser Asn Leu Arg Gln Lys Thr Leu Asp Asp Phe
        195                 200                 205

<210> SEQ ID NO 18
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Designed PCR primer to amplify a portion of
      c-ki-ras oncogene exon 1

<400> SEQUENCE: 18
ctattgttgg atcatattcg                                                20

<210> SEQ ID NO 19
<211> LENGTH: 19
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Designed PCR primer to amplify a portion of
      human c-ki-ras oncogene exon 2

<400> SEQUENCE: 19
ttcctacgga agcaagtag                                                 19

<210> SEQ ID NO 20
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Designed PCR primer to amplify a portion of
      human c-ki-ras oncogene exon 2

<400> SEQUENCE: 20
cacaaagaaa gccctcccca                                                20

<210> SEQ ID NO 21
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (13)..(15)
<223> OTHER INFORMATION: nucleotides 13 to 15 are ribonucleotides-other
      nucleotides are deoxyribonucleotides and the 3'-OH group of the
      nucleotide at 3'end is protected with amino hexyl group

<400> SEQUENCE: 21
tcgacacagc aggucaag                                                  18

<210> SEQ ID NO 22
```

```
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (13)..(15)
<223> OTHER INFORMATION: nucleotides 13 to 15 are ribonucleotides-other
      nucleotides are deoxyribonucleotides and the 3'-OH group of the
      nucleotide at 3'end is protected with amino hexyl group

<400> SEQUENCE: 22
tcgacacagc agguaaag                                                   18

<210> SEQ ID NO 23
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (13)..(15)
<223> OTHER INFORMATION: nucleotides 13 to 15 are ribonucleotides-other
      nucleotides are deoxyribonucleotides and the 3'-OH group of the
      nucleotide at 3'end is protected with amino hexyl group

<400> SEQUENCE: 23
tcgacacagc aggugaag                                                   18

<210> SEQ ID NO 24
<211> LENGTH: 19
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (17)..(19)
<223> OTHER INFORMATION: nucleotides 17 to 19 are ribonucleotides-other
      nucleotides are deoxyribonucleotides

<400> SEQUENCE: 24
acaaagaaag ccctcccca                                                  19

<210> SEQ ID NO 25
<211> LENGTH: 21
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human c-Ki-ras gene.
<220> FEATURE:
<221> NAME/KEY: misc_feature
<222> LOCATION: (16)..(18)
<223> OTHER INFORMATION: nucleotides 16 to 18 are ribonucleotides-other
      nucleotides are deoxyribonucleotides and the 3'-OH group of the
```

-continued nucleotide at 3'end is protected with amino hexyl group

<400> SEQUENCE: 25
ttgtggtagt tggagcuggt g                                              21

<210> SEQ ID NO 26
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Designed PCR primer to amplify a portion of
      human CYP2C19 gene

<400> SEQUENCE: 26
tattatctgt taactaatat ga                                             22

<210> SEQ ID NO 27
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Designed PCR primer to amplify a portion of
      human CYP2C19 gene

<400> SEQUENCE: 27
acttcagggc ttggtcaata                                                20

<210> SEQ ID NO 28
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human CYP2C19 gene.
<220> FEATURE:
<221> NAME/KEY: misc_feature
<222> LOCATION: (13)..(15)
<223> OTHER INFORMATION: nucleotides 13 to 15 are ribonucleotides-other
      nucleotides are deoxyribonucleotides and the 3'-OH group of the
      nucleotide at 3'end is protected with amino hexyl group

<400> SEQUENCE: 28
gtaagcaccc ccuggatc                                                  18

<210> SEQ ID NO 29
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide to detect the
      nucleotide substitution on human CYP2C19 gene.
<220> FEATURE:
<221> NAME/KEY: misc_feature
<222> LOCATION: (13)..(15)
<223> OTHER INFORMATION: nucleotides 13 to 15 are ribonucleotides-other
      nucleotides are deoxyribonucleotides and the 3'-OH group of the
      nucleotide at 3'end is protected with amino hexyl group

<400> SEQUENCE: 29

```
gtaagcaccc ccugaatc                                                    18

<210> SEQ ID NO 30
<211> LENGTH: 21
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Chimeric oligonucleotide primer to amplify a
      portion of human CYP2C19 gene.
<220> FEATURE:
<221> NAME/KEY: misc_feature
<222> LOCATION: (19)..(21)
<223> OTHER INFORMATION: nucleotides 19 to 21 are ribonucleotides-other
      nucleotides are deoxyribonucleotides

<400> SEQUENCE: 30
ttggtcaata tagaatttug g                                                21
```

The invention claimed is:

1. A method for detecting the presence of a base substitution at a specific base in a target nucleic acid, the method comprising:
   (1) mixing a sample containing a target nucleic acid with a Nucleotide, wherein the Nucleotide
      (A) is modified at the 3'-terminus such that extension from the terminus by a DNA polymerase does not occur;
      (B) has a base sequence capable of annealing to a region containing a specific base in the target nucleic acid; and
      (C) contains a sequence in which if there is a mismatch between the specific base and a base corresponding to the specific base in the Nucleotide in a complex composed of the Nucleotide and the target nucleic acid, the Nucleotide is not cleaved with a nuclease, and if there is no mismatch between the specific base and a base corresponding to the specific base in the Nucleotide, the Nucleotide is cleaved with a nuclease to generate a new 3'-terminus;
   (2) treating the mixture with the nuclease and the DNA polymerase; and
   (3) detecting the presence of a base substitution at the specific base in the target nucleic acid based on the presence of cleavage of the Nucleotide with the nuclease and the presence of a DNA extension reaction subsequent to the cleavage.

2. The method according to claim 1, wherein the nuclease is a ribonuclease H, and the Nucleotide contains a ribonucleotide in the region containing the base corresponding to the specific base.

3. The method according to claim 1, wherein the nuclease is a restriction enzyme, and the Nucleotide contains a recognition sequence for the restriction enzyme in the region containing the base corresponding to the specific base.

4. The method according to claim 1, wherein the Nucleotide has a sequence in which if there is no base substitution in the target nucleic acid, a mismatch is not generated in the complex composed of the Nucleotide and the target nucleic acid.

5. The method according to claim 1, wherein the Nucleotide has a sequence in which if there is a base substitution in the target nucleic acid, a mismatch is not generated in the complex composed of the Nucleotide and the target nucleic acid.

6. The method according to claim 1, wherein the cleavage of the Nucleotide is detected based on the presence of an extension product generated by the action of the DNA polymerase.

7. The method according to claim 1, wherein the cleavage of the Nucleotide is detected based on the presence of a fragment of a 3' portion released from the Nucleotide generated by the action of the nuclease.

8. The method according to claim 1, wherein the cleavage of the Nucleotide is detected using a labeled compound attached to the Nucleotide.

9. The method according to claim 8, wherein the labeled compound is attached to the Nucleotide in a portion 3' to the cleavage site for the nuclease.

10. The method according to claim 8, wherein the labeled compound is attached to the Nucleotide in a portion 5' to the cleavage site for the nuclease.

11. The method according to claim 8, wherein the labeled compound attached to the Nucleotide is a fluorescent substance.

12. The method according to claim 11, wherein a substance capable of quenching fluorescence is further attached to the Nucleotide, and the fluorescence is emitted upon cleavage by the nuclease.

13. The method according to claim 11, wherein the cleavage of the Nucleotide is detected by a fluorescence polarization method.

14. The method according to claim 1, wherein the Nucleotide is modified at the 3'-terminus by modification of the hydroxyl group at the 3-position of ribose.

15. The method according to claim 1, wherein the Nucleotide contains a nucleotide analog and/or a modified nucleotide.

16. The method according to claim 15, wherein the nucleotide analog is a deoxyriboinosine nucleotide or a deoxyribouracil nucleotide, and the modified nucleotide is an ($\alpha$-S) ribonucleotide.

17. The method according to claim 1, further comprising a step of nucleic acid amplification in which an extension product generated by the action of the DNA polymerase is used as a template.

18. A method for analyzing a genotype of an allele, the method comprising detecting the presence of a base substitution at a specific base in a target nucleic acid according to the method defined by claim 17.

* * * * *